(12) United States Patent
Pasquino et al.

(10) Patent No.: US 10,806,577 B2
(45) Date of Patent: Oct. 20, 2020

(54) ATRIO-VENTRICULAR VALVE STENT WITH NATIVE LEAFLET GRASPING AND HOLDING MECHANISM

(71) Applicant: Epygon

(72) Inventors: Enrico Pasquino, Savigny (CH); Marcio Scorsin, Luxembourg (LU); Stefano Pasquino, Savigny (CH); Andrea Marchisio, Ivrea (IT); Lorenzo Valerio, Moriago della Battaglia (IT); Sergio Casalegno, San Mauro Torinese (IT); Marco Gard, Borgomasino (IT); Pietro Arru, Marentino (IT)

(73) Assignee: Epygon, Paris (FR)

( * ) Notice: Subject to any disclaimer, the term of this patent is extended or adjusted under 35 U.S.C. 154(b) by 34 days.

(21) Appl. No.: 15/576,804

(22) PCT Filed: Jun. 3, 2016

(86) PCT No.: PCT/EP2016/062663
§ 371 (c)(1),
(2) Date: Nov. 25, 2017

(87) PCT Pub. No.: WO2016/193437
PCT Pub. Date: Dec. 8, 2016

(65) Prior Publication Data
US 2018/0303612 A1   Oct. 25, 2018

(30) Foreign Application Priority Data

Jun. 4, 2015  (EP) .................................... 15170736
Feb. 5, 2016  (WO) ................. PCT/EP2016/052452

(51) Int. Cl.
*A61F 2/24*  (2006.01)

(52) U.S. Cl.
CPC .......... *A61F 2/2448* (2013.01); *A61F 2/2418* (2013.01); *A61F 2210/0014* (2013.01);
(Continued)

(58) Field of Classification Search
None
See application file for complete search history.

(56) References Cited

U.S. PATENT DOCUMENTS 8,585,755 B2    11/2013   Chau et al.
8,685,086 B2    4/2014    Navia et al.
(Continued)

FOREIGN PATENT DOCUMENTS

CN       103974674 A      8/2014
EP         2282700 B1      2/2011
(Continued)

OTHER PUBLICATIONS

International Search Report of PCT/EP2016/062663 dated Aug. 31, 2016.
(Continued)

*Primary Examiner* — Leslie Lopez
(74) *Attorney, Agent, or Firm* — Andre Roland S.A.; Nikolaus Schibli

(57) ABSTRACT

Atrio-ventricular valve stent (1) having a tubular shape, with a sub annular anterior side (2), a sub annular posterior side (3) and sub annular lateral sides (13), the sub annular anterior side (2) comprising a self-folding native leaflet engagement member (4-9) that forms a straight extension of said sub annular anterior side (2) when the stent (1) is collapsed and that is folded on itself when the stent (1) is in an expanded state; said engagement member (4-9) forming an integral part of the stent (1) and wherein each sub annular lateral side (13) is longer than said sub annular anterior side (2) when the stent (1) is in an expanded state.

28 Claims, 34 Drawing Sheets

(52) U.S. Cl.
CPC ............... *A61F 2220/0016* (2013.01); *A61F 2230/0034* (2013.01)

(56) References Cited

U.S. PATENT DOCUMENTS

| | | | |
|---|---|---|---|
| 9,039,757 B2 | 5/2015 | McLean et al. | |
| 9,173,737 B2 | 11/2015 | Hill et al. | |
| 9,333,075 B2 | 5/2016 | Biadillah et al. | |
| 9,510,943 B2 | 11/2016 | Mesana et al. | |
| 9,532,868 B2 | 1/2017 | Braido | |
| 9,572,660 B2 | 2/2017 | Braido et al. | |
| 10,149,759 B2 | 12/2018 | Naor | |
| 10,278,814 B2 | 5/2019 | Scorsin et al. | |
| 2006/0259135 A1 | 11/2006 | Navia et al. | |
| 2010/0298931 A1* | 11/2010 | Quadri | A61F 2/2418 623/2.11 |
| 2011/0004299 A1* | 1/2011 | Navia | A61F 2/2418 623/2.18 |
| 2011/0208297 A1* | 8/2011 | Tuval | A61F 2/2418 623/2.17 |
| 2014/0249622 A1 | 9/2014 | Carmi et al. | |
| 2014/0257467 A1 | 9/2014 | Alne et al. | |
| 2014/0324164 A1 | 10/2014 | Gross et al. | |
| 2015/0142100 A1 | 5/2015 | Morriss et al. | |

FOREIGN PATENT DOCUMENTS

| | | |
|---|---|---|
| RU | 139021 U1 | 4/2014 |
| WO | WO 2006/113906 | 10/2006 |
| WO | WO 2008/091515 | 7/2008 |
| WO | WO 2008/150529 | 12/2008 |
| WO | WO 2009/045338 | 4/2009 |
| WO | WO 2011/069048 | 6/2011 |
| WO | WO 2011/002996 | 11/2011 |
| WO | WO 2013/160439 | 10/2013 |
| WO | WO 2014/144937 | 9/2014 |
| WO | WO2014144937 A2 | 9/2014 |
| WO | WO 2014/181336 | 11/2014 |

OTHER PUBLICATIONS

Written Opinion of the International Search Authority for PCT/EP2016/062663 dated Aug. 31, 2016.
Opposition filed at the European Patent Office on May 20, 2019 for the counterpart application EP16732955.6, EP Patent No. EP3302364.
Chinese Office Action and its English translation for Application CN201680032640.8 dated Apr. 23, 2019.
PCT/EP2016/062663—IPRP patentability report EN dated Dec. 5, 2017.
Rusian Office Action issued by the RUPTO for Application RU 2017146388 dated Aug. 15, 2019.
Search report issued by the RUPTO for Application RU 2017146388 dated Aug. 15, 2019.

* cited by examiner

Figure 30 A
Figure 30 B
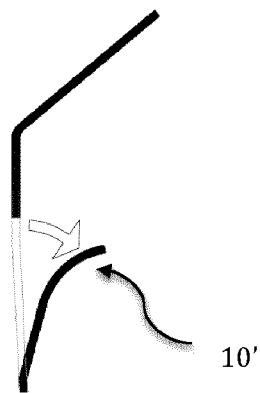
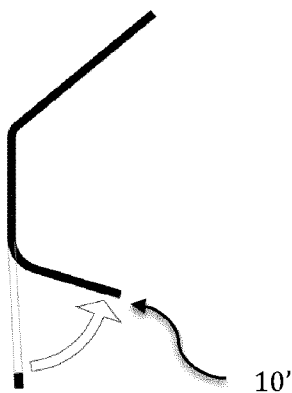
Figure 31 A
Figure 31 B
Figure 31 C
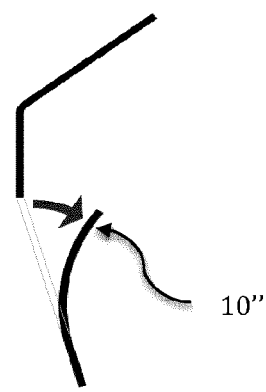
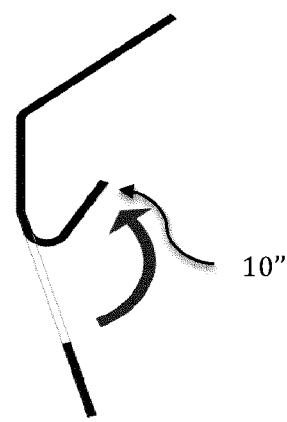
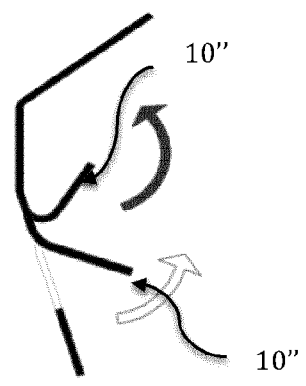

Figure 41 A
Figure 41 B
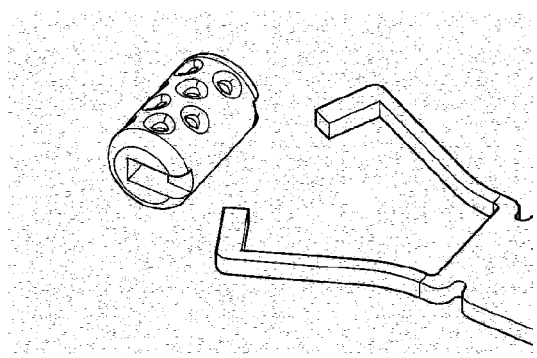
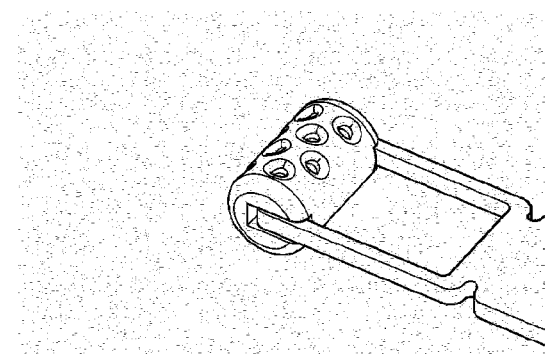
Figure 42 A
Figure 42 B
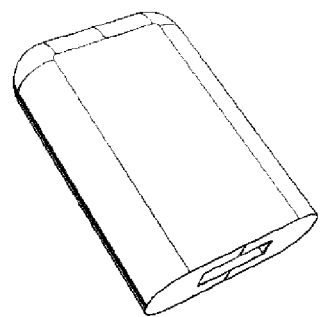
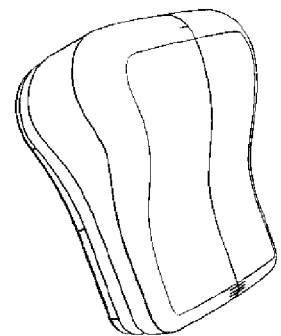
Figure 42 C
Figure 42 D
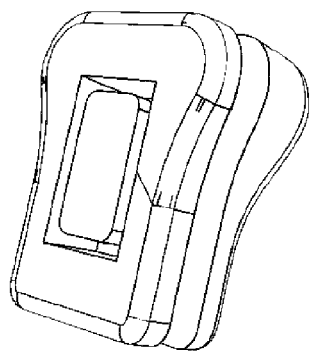
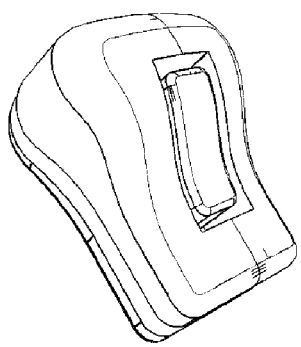

Figure 51 A
Figure 51 B
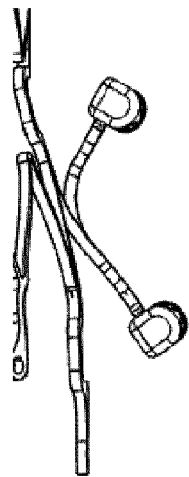
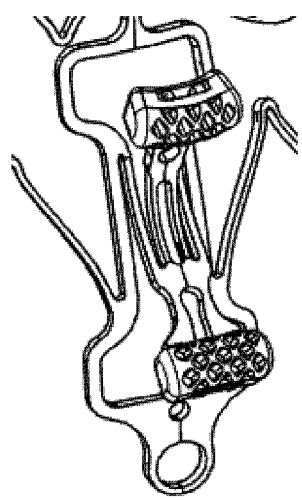
Figure 52 A
Figure 52 B
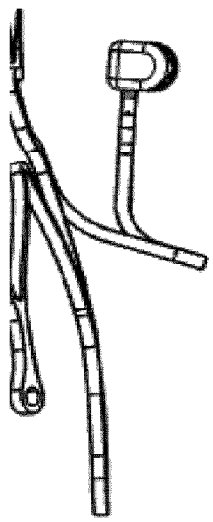
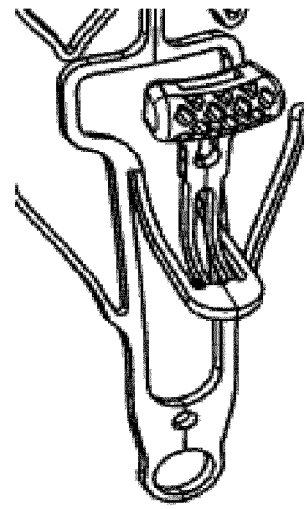

Figure 53 A
Figure 53 B
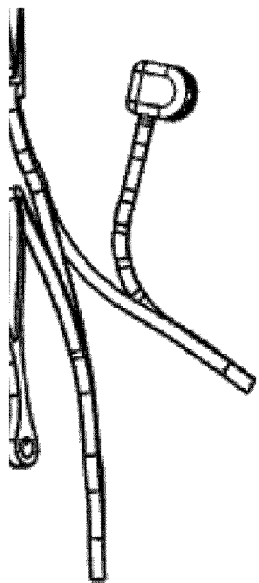
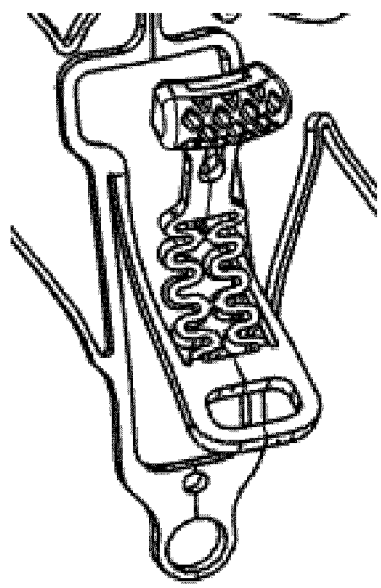
Figure 54 A
Figure 54 B
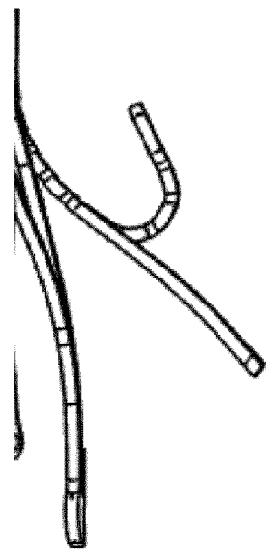
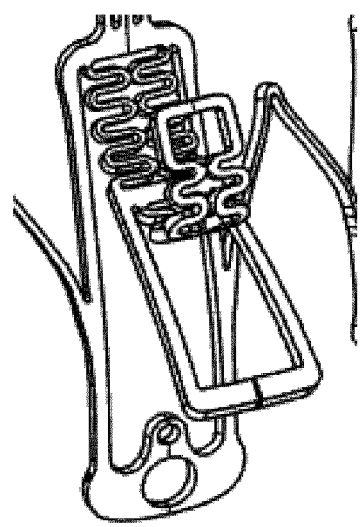

ATRIO-VENTRICULAR VALVE STENT WITH NATIVE LEAFLET GRASPING AND HOLDING MECHANISM

CROSS REFERENCE TO RELATED APPLICATIONS

The present application is a United States national stage application of International patent application PCT/EP2016/062663 filed on Jun. 3, 2016 designating the United States, and claims foreign priority to International patent application PCT/EP2016/052452 filed on Feb. 5, 2016, and also claims foreign priority to European patent application EP 15170736.1 filed on Jun. 4, 2015, the contents of all three documents being herewith incorporated by reference in their entirety.

FIELD OF INVENTION

The present invention refers to heart valve stents, in particular atrio-ventricular valve stents that comprise a native leaflet locking mechanism and/or an anchoring system to the cardiac tissue.

STATE OF THE ART

Mitral valve (see FIG. 1) is not only a valve but also a part of the left ventricle. The mitral apparatus includes the papillary muscles, the tendinous chordae, the two leaflets and the mitral annulus, which altogether work as a valve. Anatomically, the anterior segment of the mitral annulus between the two commissures or the two trigones (⅓ of the mitral annulus length) doesn't move. The posterior segment of the mitral annulus (⅔ of the mitral annulus length), on the contrary, moves accordingly to the left ventricle contraction.

It is well known that open-heart mitral valve surgery induces a high risk of morbidity and mortality, one of the main reasons is that mitral valve disease may be the cause or the consequence of left ventricular failure and surgery in patients with damaged cardiac function carries high mortality. From the technical point of view when a valve replacement is performed, the native mitral valve is either resected or, if not resected (to preserve the ventricular function), the leaflets are blocked by the sutures to allow the heart prosthesis work properly and not be disturbed by the subvalvular apparatus.

One promising alternative to open heart surgery is the valve replacement trough transcatheter technique, i.e. the prosthesis is comprising a stent that is introduced in a collapsed state through a catheter. In the present document, "stent" and "valve stent" refer to the same object. The stent expands when it leaves the catheter, just before reaching its definitive position, and occupies the previous valvular site without the help of surgical stitches as in standard surgical technique.

Therefore, the safety and efficacy of the mitral transcatheter heart valve prosthesis is strictly linked to its anchoring system to the anatomical structures. The pressure peak during systolic time can be higher than 200 mmHg therefore the expulsive forces applied to the valve are important, to such an extent that they can displace the prosthesis into the left atrium.

The anchoring systems so far developed for atrio-ventricular prostheses, are based on various ideas among them hooks grabbing the mitral annulus or anchors grabbing the anterior and/or the posterior leaflets or the mitral trigones. Other solutions include a sort of neo-chordae anchoring the prosthesis to the external surface of left ventricle's apex. With the objective of simplification, two types of different approaches have been identified; the invasive anchoring and the anatomical anchoring.

The invasive approach seeks to anchor trough hooks that come out of the stent and penetrate the cardiac tissue at the annular or sub-annular level. The idea is to mimic the surgical sutures to keep the valve in place. The main advantages of this method are that the prosthesis may have a low ventricular profile because they don't need to use the mitral apparatus or capture the mitral leaflets to be anchored, therefore reducing the risk of creating a left ventricular obstruction tract, and therefore can be deployed either from the apex of the left ventricle (retrograde) or from the left atrium (anterograde). However, there are three major disadvantages using this approach; (i) it is well known that the left atrium is associated with thromboembolic events especially in patients with mitral disease and atrial fibrillation, it sounds logical that the large atrial protrusion of this type of valve may increase the risk of this complication; (ii) low profile ventricular valves are often associated with high-risk perivalvular leakage due to the limited area of attachment between the valve stent and the annular/ventricular tissue and (iii) the presence of chronic inflammation due to the hooks' tissue penetration that can facilitate secondary infection (endocarditis).

The anatomic approach seeks to anchor the valve stent by taking advantage of the anatomic characteristics of the mitral valve, namely the leaflets and their chordae, the fibrous trigones, and the posterior sub-annular groove. The idea is to place less traumatic engagement members or flat blades or extension bodies precisely at those anatomical elements to keep the stent in place. The systolic pressure promotes over a mitral prosthesis an expulsion force that may lead to tissue damage and valvular displacement. The main idea is to place as much as anchoring structures as possible to better distribute the force. The main advantages of this approach are that in theory it causes less damage to the cardiac tissue and frequently capture mitral leaflets which helps either the anchoring and also to prevent obstruction of the ventricular flow. Capturing the leaflets has additional advantages. It keeps under tension the mitral valve apparatus (tendinous chordae and papillary muscles) during systole thus preventing ventricular remodelling and dilatation. This is a very important aspect because one of the greatest benefits of transcatheter mitral valve would be in patients with poor left ventricular function, therefore it is relevant to maintain the integrity of the mitral valve apparatus to preserve the ventricular function.

When transcatheter mitral valve prosthesis is used to replace the native valve, resection is not feasible and the native valve must stay in place. One of the main issues in transcatheter mitral valve implantation is that the presence of the native anterior leaflet (which has no use anymore) may obstruct the left ventricle outflow tract (LVOT). Indeed, by implanting a stent in the mitral position, the metallic structure creates a radial force to secure the valve in place, consequently pushing the anterior leaflet of the mitral valve towards the aortic valve, may potentially cause an obstruction of the LVOT. One strategy to overcome this problem is to positioning the stent very high, i.e. upstream, above the annular plane so as the ventricular part can be very short. Although, the atrialization of the prosthesis could eventually reduce the risk of LVOT obstruction, it increases the risk of atrial thrombosis and embolism.

Another solution is to create engagement members, as disclosed for instance in US patent application US 2011/

208297 A1, to catch and block the native valve leaflets. However, even though an engagement member could efficiently block the mitral leaflets, the more the stent protrudes deep into the ventricle, the higher is the risk of LVOT obstruction. This risk is particularly elevated in some examples disclosed in US 2011/2008297 A1 where the height of the anterior stent side may be longer than the height of the posterior side.

Providing a stent anterior side of the same height of the posterior side when collapsed into a catheter, but ultimately having a shorter height than the posterior side, after being released from the catheter, has already been proposed by the inventors, as disclosed in international patent application WO 2013/160439 A1. This prior art also discloses an anterior native leaflet locking mechanism. Initially the stent is symmetric and is made of a memory shape material. The anterior side is thermally everted (pre-shaped in everted position and distended when the stent is in collapsed state) and forms an engagement member for the anterior native leaflet.

Although innovative this latest solution is however not entirely satisfactory. Everting the complete stent anterior side may negatively affect the stent properties in this region. The stent may be too rigid and/or too thick. This inconvenient also occurs at any symmetric or asymmetric segment of any stent, anterior, posterior or lateral.

As explained previously, there are many issues related to the stent shape and length, as well as the best anchoring system that take into account the morphology and the physiology of the mitral valve.

There is, therefore, a need to improve the existing atrio-ventricular valve stents.

GENERAL DESCRIPTION OF THE INVENTION

The problems mentioned in the previous chapter are overcome with the atrio-ventricular valve stent according to the invention.

The stent according to the invention may be advantageously used, but not exclusively, for replacement of the mitral valve.

More precisely the invention concerns an atrio-ventricular valve stent having a tubular shape, with a sub annular anterior side, a sub annular posterior side and sub annular lateral sides, the sub annular anterior side comprising a self-folding native leaflet engagement member that forms a straight extension of said sub annular anterior side when the stent is collapsed and that is folded on itself when the stent is in an expanded state; said engagement member forming an integral part of the stent and wherein each sub annular lateral side is longer than said sub annular anterior side when the stent is in an expanded state.

In the present document the expression "anterior side" or "stent anterior side" refers to the stent side that is directly facing the aortic valve when the stent is oriented in its definitive position within the native valve complex. The "posterior side" refers to the stent side that is opposite to the anterior side.

The expression "sub annular" refers to a stent region that is below the annulus and within the ventricle, when the stent is located in its definitive position.

The valve stent, when deployed according to the invention, is preferably shorter at the sub annular anterior side in order to reduce the risk of obstruction of the LVOT.

The valve stent, when deployed, may be longer at the posterior side in order to obtain a better anchoring of the valve during systole.

The stent according to the invention may also be shorter at the sub annular posterior side to reduce the contact between the stent and the posterior ventricular wall, therefore reducing the risk of stent fracture overtime.

In a preferred embodiment, in the collapsed state, the sub annular anterior side height added to the engagement member length may be equivalent, shorter or longer than the sub annular height of the posterior side (in case the posterior side were shorter than the total stent length). The presence of the engagement member however, does not increase the total stent length in the collapsed state because it comes from inside the stent structure. This embodiment offers two important advantages. First, by not increasing the length of the stent and consequently the length of the delivery system necessary to release the valve, it facilitates a transcatheter approach through an antegrade (e.g. from the left atrium) access where the path to reach the mitral position is not straight. Longer is the stent and consequently longer is the valve cover of the delivery system, less is the possibility to reach the mitral valve trough a trans-femoral approach. The second main advantage is that having the same ventricular length, in a collapsed state, allows retaining the valve inside the valve cover of the delivery system when the implant access is retrograde (e.g. from the left ventricle).

In another embodiment, in the collapsed state, the sub annular anterior side height added to the engagement member length may be equivalent to the height of the posterior side in case an engagement member is present also in the posterior side to catch the posterior leaflet.

When the stent is released, the engagement (s) member bends, at least 90° (preferably 160-180°). This creates an empty space at the anterior side and consequently it does not obstruct the ventricular flow and at the same time the anterior leaflet is grasped and taken away from the ventricular outflow tract. As far as the posterior engagement member is concerned, the posterior empty space created by the rotation of the posterior engagement member reduces the contrast between the posterior left ventricle wall and the stent.

In another embodiment the engagement member(s) bends of 180°, or close to that value, when the stent is released. The bending angle is predefined when the stent is manufactured.

Preferably the engagement member(s) is/are made of a memory shape material. In this case the bending angle is thermally shaped.

In another embodiment, the engagement member(s) is forming an integral part of the stent.

Advantageously there is only one single point that links the engagement member to the stent anterior/posterior side.

In another embodiment the engagement member(s) is/are provided with a specific geometry containing at least one wavy line. Such a configuration allows a bending with a minimal torsion that avoids the damage of the metal crystalline structure and preserves the superelastic characteristics of the memory shape material.

In another embodiment the stent comprises a native leaflet locking system. Advantageously this locking system is defined by at least one extensions body, preferably two, bent out of preferably 30° from the stent structure. The locking system works in grabbing and retaining the native leaflet impeding its interference with the LVOT and providing thereby an efficient anterior anchoring to the valve. The locking mechanism is based on the sequence of events occurring during the release of the stent from the catheter. Initially the extension bodies are released and open, e.g. at 30°. Then the engagement member is released and bends out to a predefined angle, usually between 160-180°, in a way that moving upward the rim of the anterior mitral leaflet it allows the extension bodies to retain the native leaflet. Finally the native leaflet is pinched and retained between the extension bodies and the engagement members.

In another embodiment according to the invention the stent comprises one anterior and one posterior engagement members, which respectively block the anterior and the posterior mitral leaflets, both engagement members being located on the stent sub annular edge. The length of the anterior and posterior mitral leaflets is different. The anatomic distance between the anterior mitral annulus and the free edge of the anterior leaflet (middle of A2) is around 28 mm. The distance between the posterior mitral annulus and the edge of the posterior leaflet (P2) is around 20 mm. In case two engagement members are used to block both leaflets, they may be released at different level in the sub-annular stent structure. The anterior engagement member may be released further down because it needs to grab a longer leaflet. Otherwise, the posterior engagement member may be released at a higher level because it needs to grab a shorter leaflet.

To prevent any traumatic damage of leaflet(s) tissue, sleeves can be used to cover the engagement member(s). For the same purpose to prevent damages to the cardiac tissue the distal end of the engagement members can be protected by protection caps.

In some embodiments in addition to the engagement member(s) and with the objective to further increase the anchoring of the stent, at least two or more extension bodies fixed to the stent annular zone, i.e. not to the bottom of the ventricular part of the stent are placed below the mitral annulus to secure the stent in place. This type of anatomic anchoring can be perfectly and safely used in both retrograde and antegrade approach because systematically capture mitral leaflets.

To prevent any traumatic damage of cardiac tissue, protection caps can be used to cover the distal end of extension bodies, which is in contact with the surrounding tissue, thus preventing tissue damage and also increasing the contact surface area. Having a larger area of anchoring further improves the stability of the stent and helps to better distribute the expulsion forces during ventricular systole.

In other embodiments the anatomic anchoring is obtained with an extension body from the annular part that are designed to be placed at the trigones, together with an extension body coming from the bottom of the ventricular part of the stent. This extension body can be either non-traumatic or partially traumatic depending on the presence of protection caps.

In other embodiments the anatomic anchoring is obtained with an extension body from the annular part that are designed to be placed at the trigones, together with two extension bodies coming from the annular part of posterior segment of the stent. This extension body/ies can be either non-traumatic or partially traumatic depending on the presence of protection caps. Two engagement members, the anterior that captures the anterior leaflet acting in both ways, anchoring and preventing LVOT obstruction in a similar way the posterior engagement member also has a double function, capture the posterior leaflet and in its final position is placed below the atrial groove as an additional anchor. These two engagement members can also be associated to the four extension bodies. This embodiment has therefore seven points of anchoring.

Advantageously the extensions bodies are forming an integral part of the stent, i.e. they are directly obtained from the stent frame. This avoids the additional anchoring structures placed below (beyond) the defined profile of the stent (the distal end of the stent) and bent out of 100 to 180°, or external structures added by welding or mechanical grip that are overlapping the stent structure. Preferably the extension bodies according to the invention come from the stent frame, therefore do not increase the stent length, and do not increase the stent thickness in collapsed configuration, both major features for a transcatheter valve.

DETAILED DESCRIPTION OF THE INVENTION

The invention is discussed below in a more detailed way with examples illustrated by the following figures.

Figure 2:
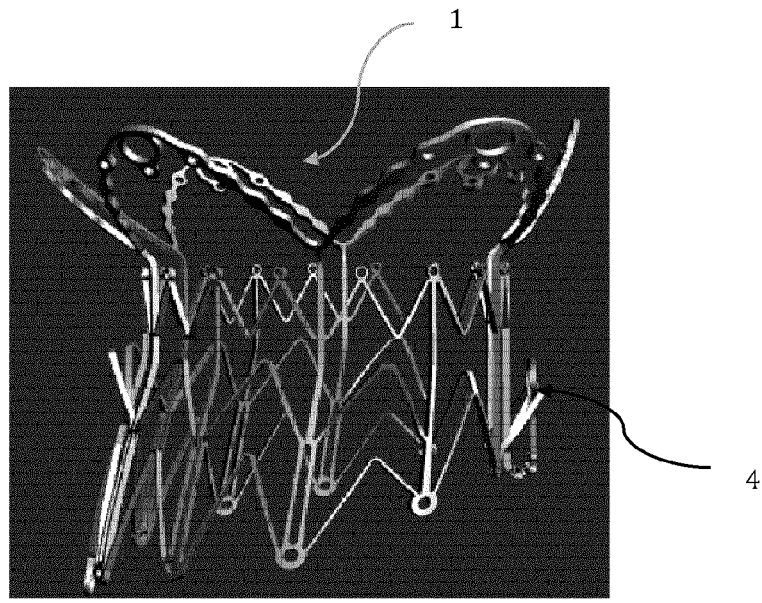
FIG. 2 shows an example of a mitral valve stent according to the invention.
Figure 3:
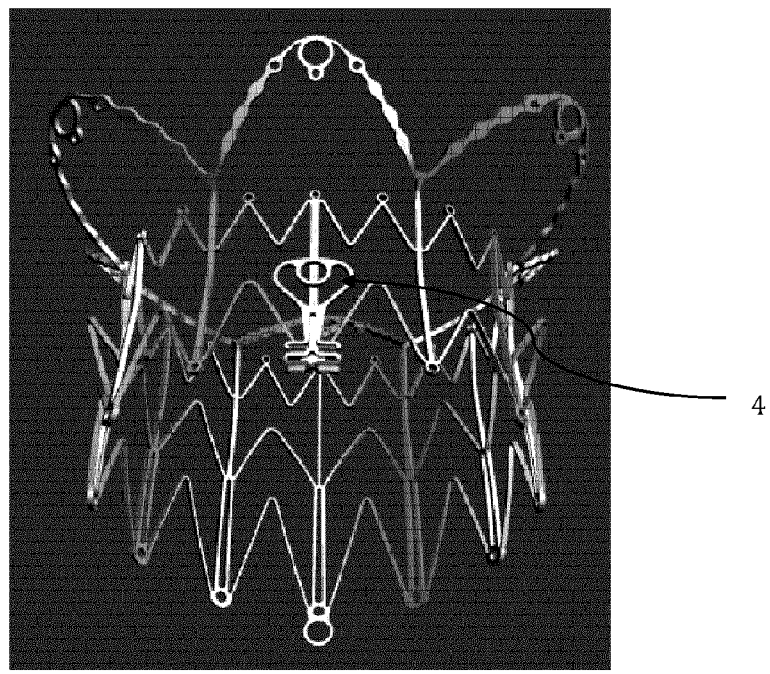

FIG. 3 better shows the anterior side of the stent of FIG. 2.

Figure 4:
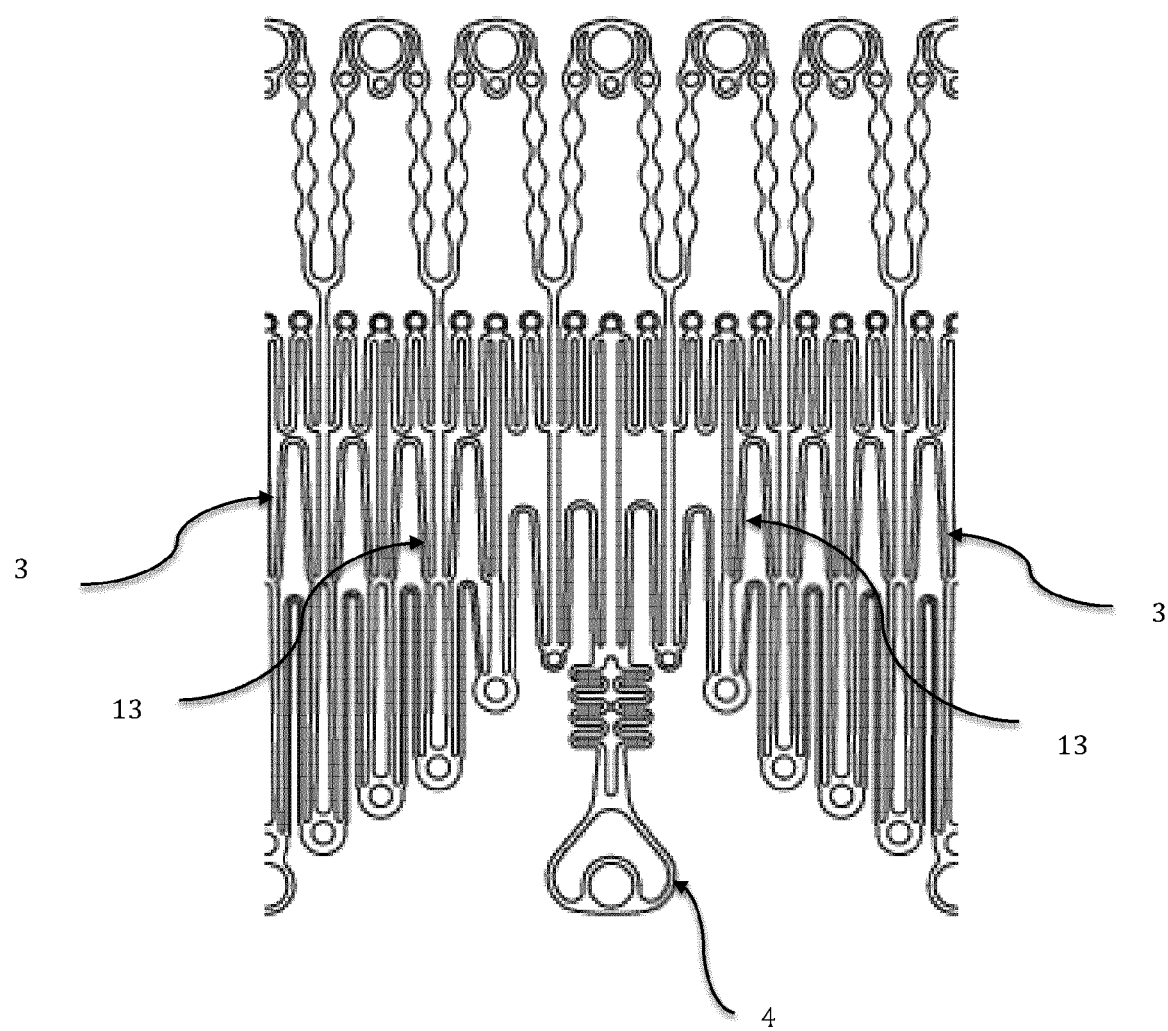

FIG. 4 shows a portion of a stent according to the invention, in a flat configuration.

Figure 5:
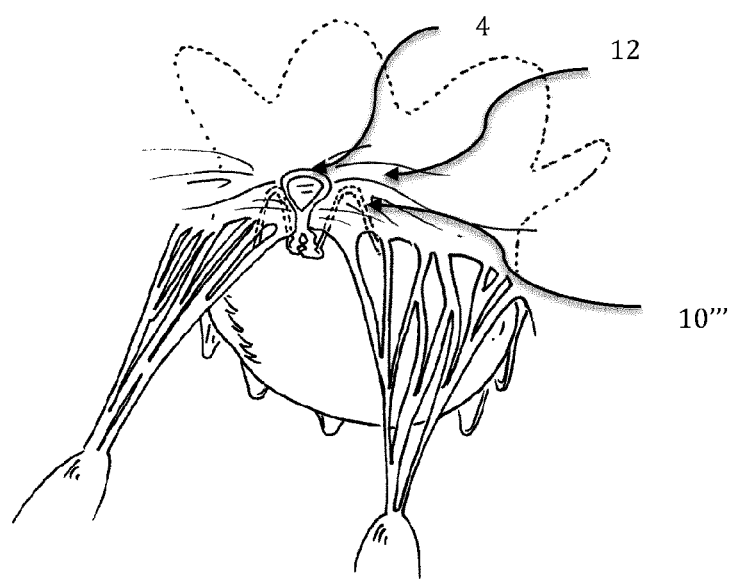

FIG. 5 represents native leaflet retained by a stent according to the invention.

Figure 6:
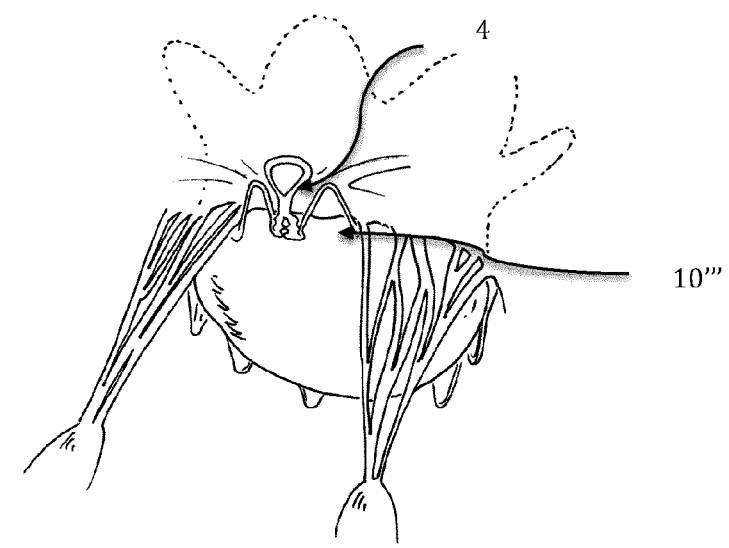

FIG. 6 represents the leaflet of FIG. 5 in a locked position.

Figure 7:
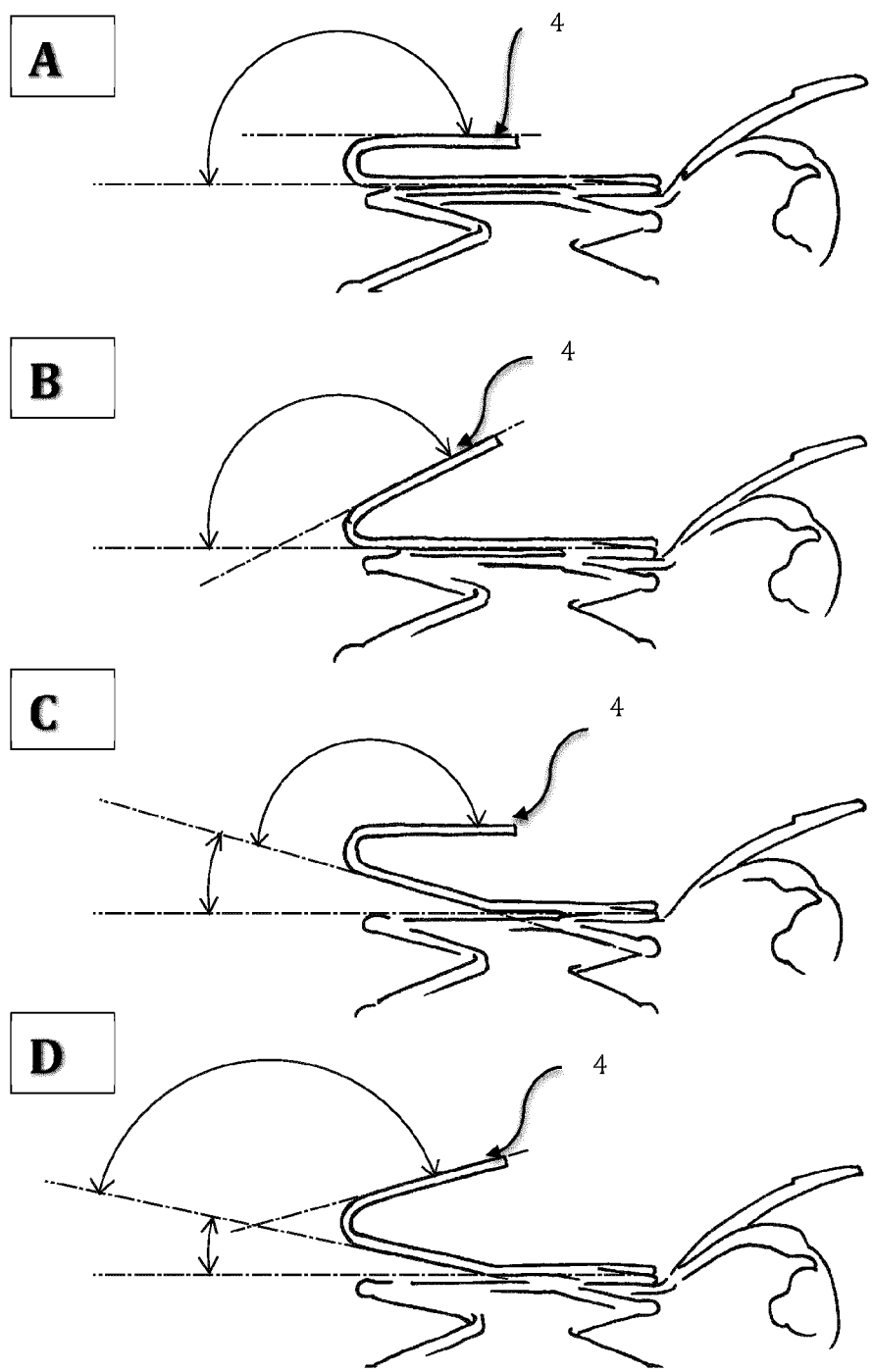

FIG. 7 shows different orientations of an engagement member according to the invention.

Figure 8:
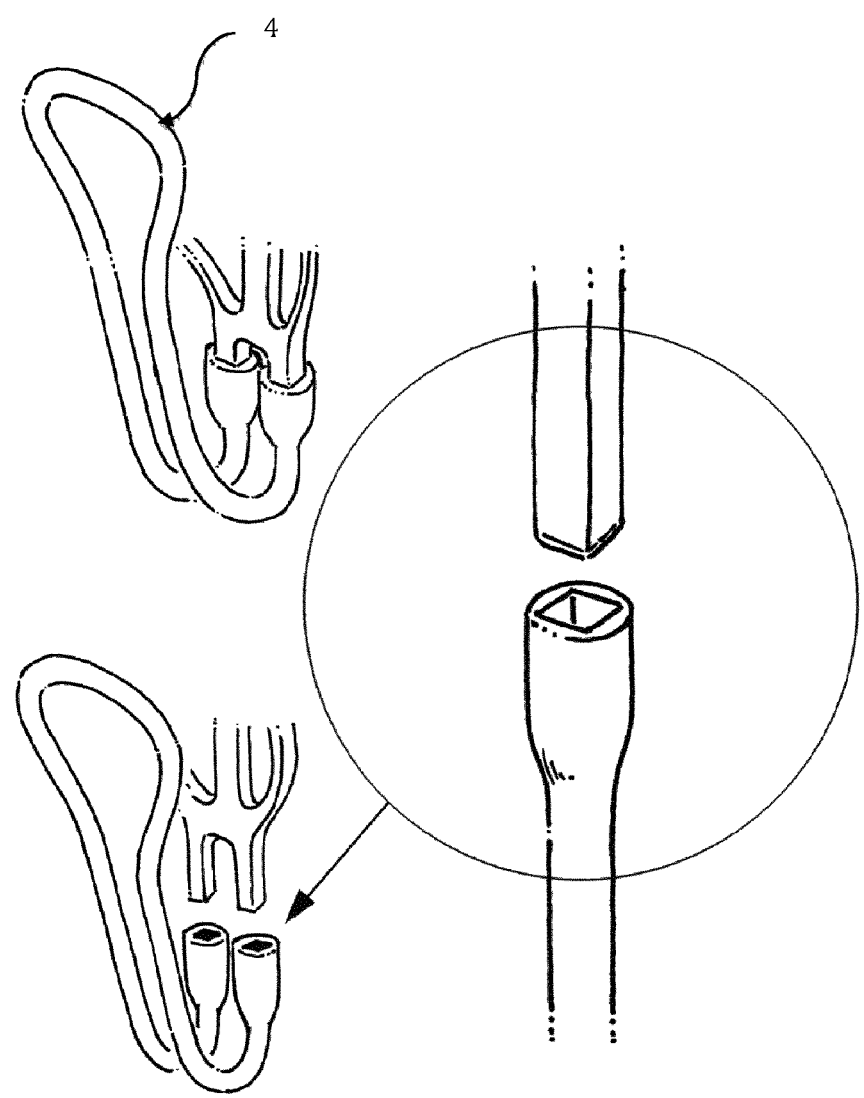

FIG. 8 illustrates another example showing the fixation of an engagement member to the stent body.

Figure 9:
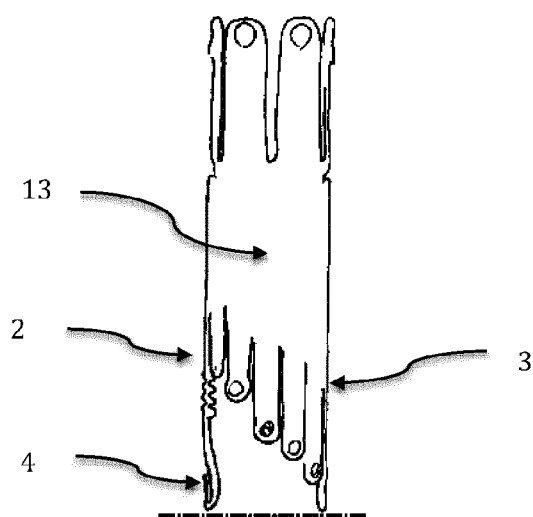

FIG. 9 shows a stent according to the invention in a collapsed state with only one anterior engagement member.

Figure 10:
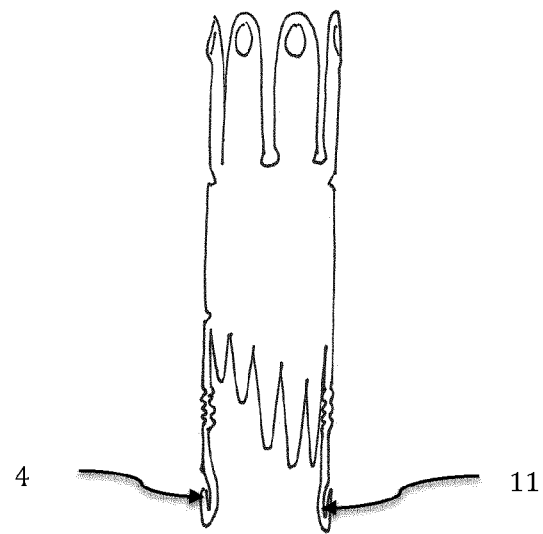

FIG. 10 shows a stent according to the invention in a collapsed state with both one anterior and one posterior engagement members.

Figure 11:
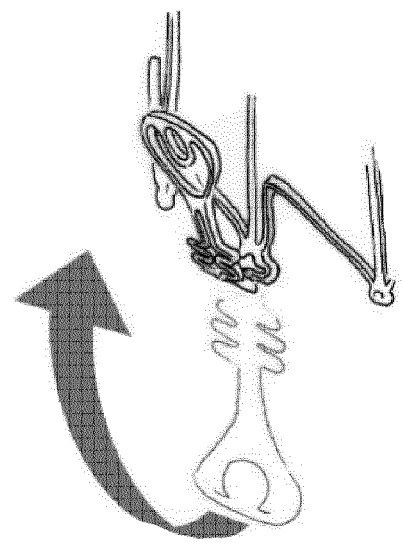

FIG. 11 illustrates an example of the movement of an engagement member according to the invention, in an intermediate position.

Figure 12:
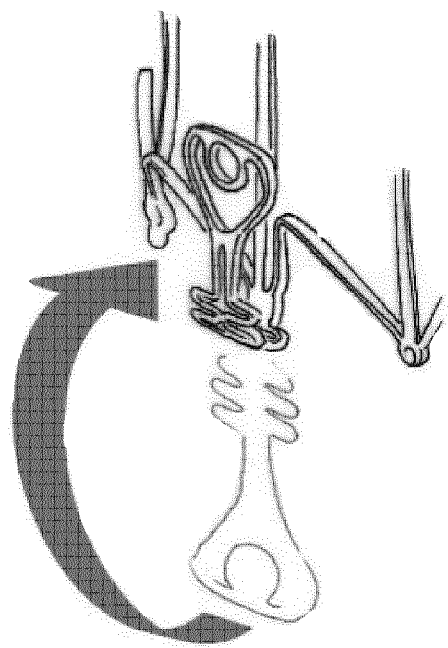

FIG. 12 shows the engagement member of FIG. 11 in a final position.

Figure 13A:
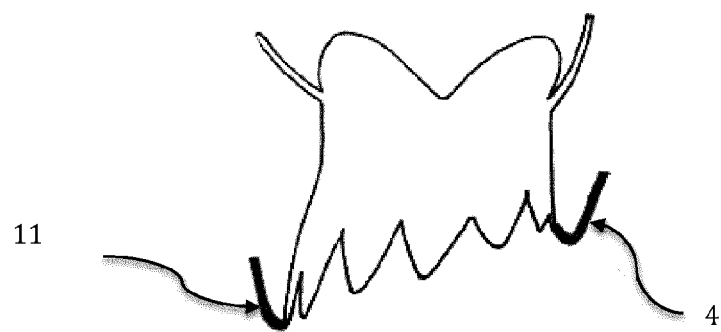

FIG. 13A is a schematic representation of a stent according to the invention with one anterior and one posterior engagement members.

Figure 13B:
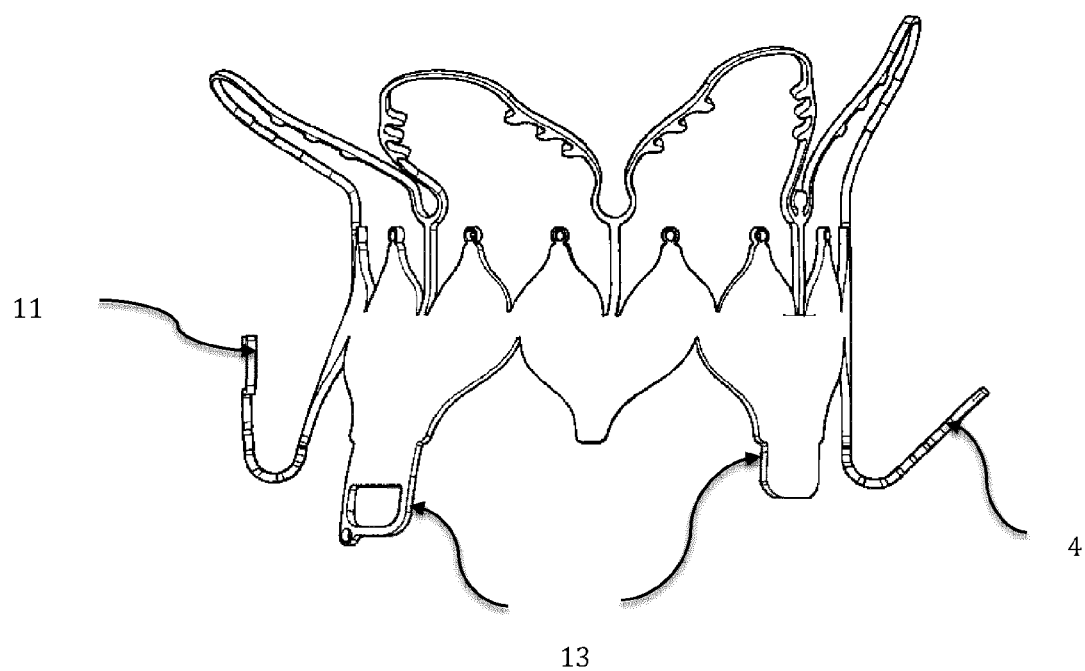

FIG. 13B shows another configuration of a posterior engagement member originating at the sub-annular segment of the stent.

Figure 14:
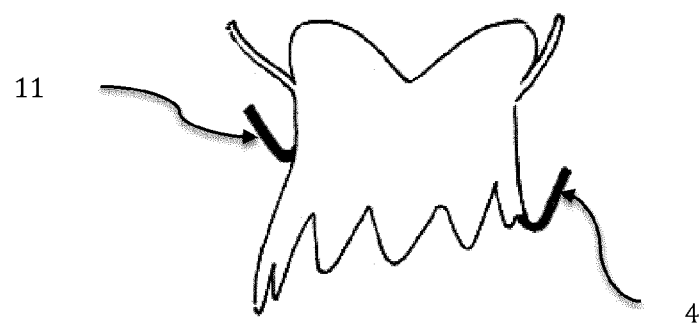

FIG. 14 is a schematic representation of another stent according to the invention.

Figure 15:
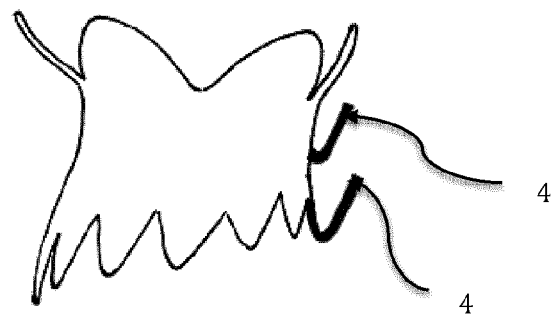

FIG. 15 is a schematic representation of another stent according to the invention.

Figure 16:
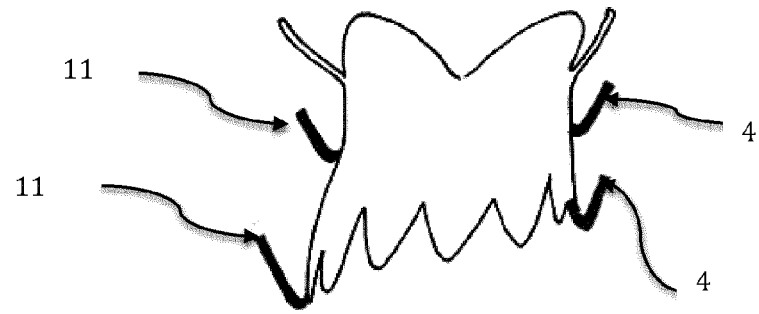

FIG. 16 is a schematic representation of another stent according to the invention.

Figure 17:
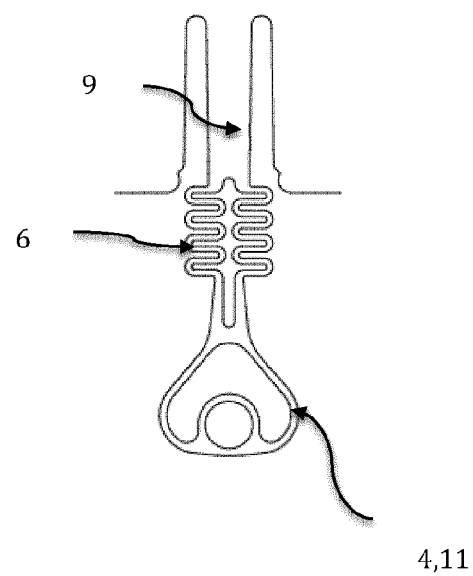

FIG. 17 shows another engagement member according to the invention.

Figure 18:
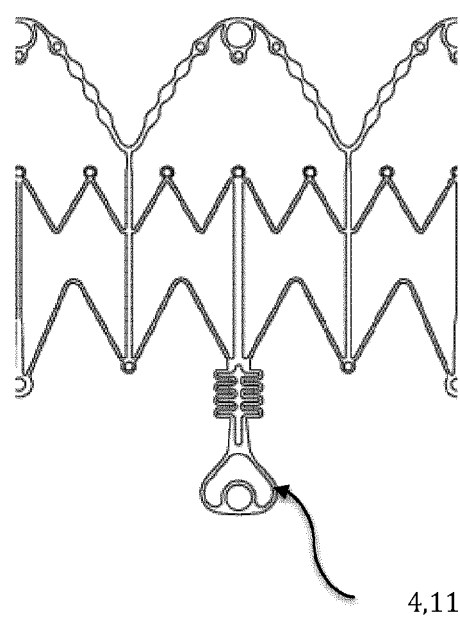

FIG. 18 shows another engagement member according to the invention, together with a stent portion.

Figure 19:
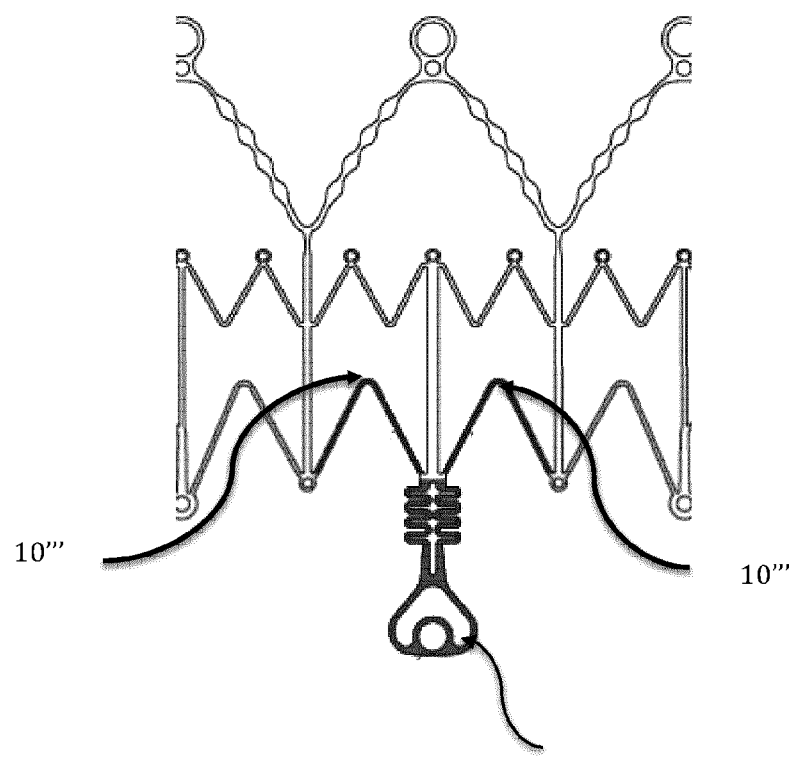

FIG. 19 shows the engagement member of FIG. 18 with the locking system in bold.

FIGS. 20 to 26 show other examples of engagement members according to the invention.

Figure 27:
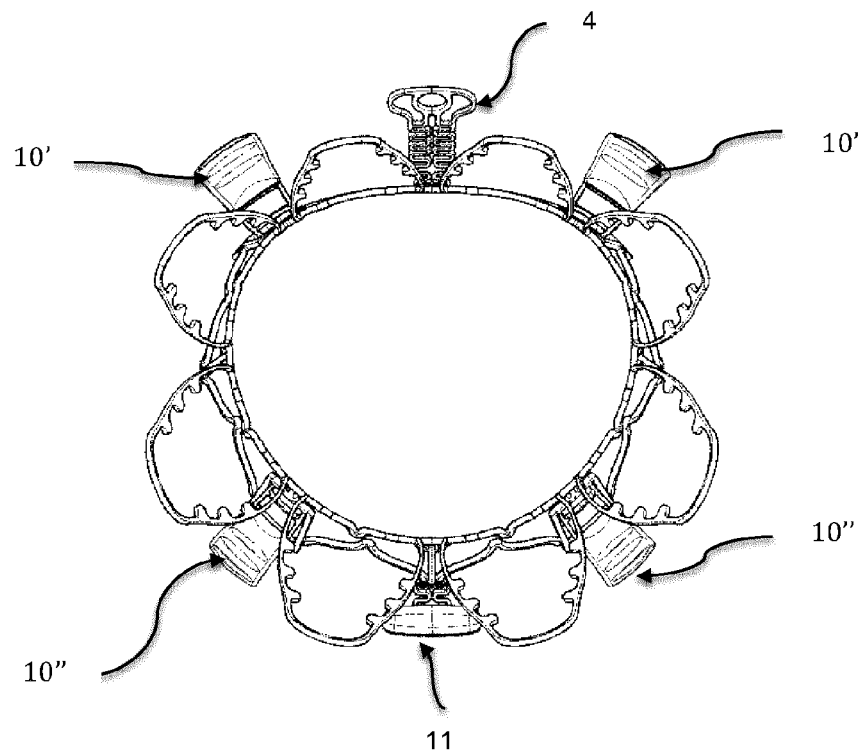

FIG. 27, shows an example of a mitral valve stent according to the invention with two engagement members anterior and posterior, two extension bodies at the anterior side to be placed at the trigones and two posterior extension bodies.

Figure 28:
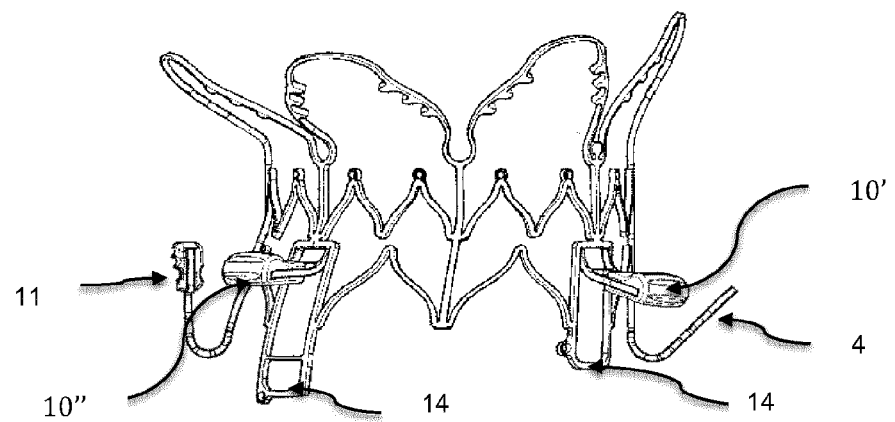

FIG. 28, shows another example of a mitral valve stent according to the invention with two engagement members anterior and posterior, two extension bodies coming out from a stent frame.

Figure 29:
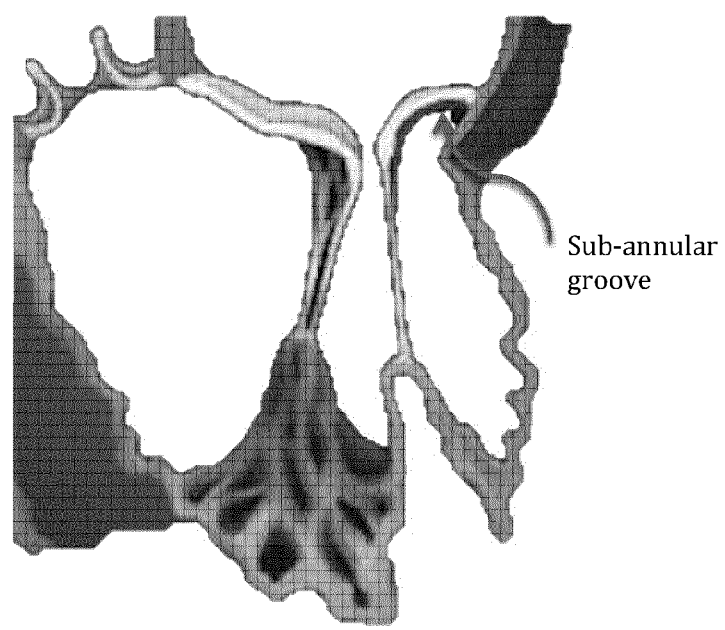

FIG. 29 is an anatomical representation showing the sub annular groove.

FIGS. 30A and 30B show examples of trigones extension bodies.

FIGS. 31A to 31C show examples of posterior extension bodies.

FIGS. 32A to 32D show examples of extension bodies.

Figure 33:
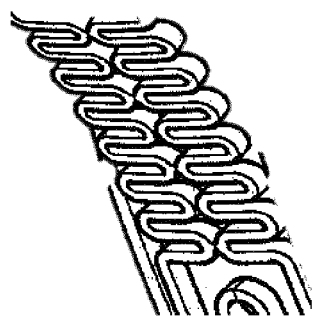

FIG. 33 illustrates two wavy lines.

Figure 34:
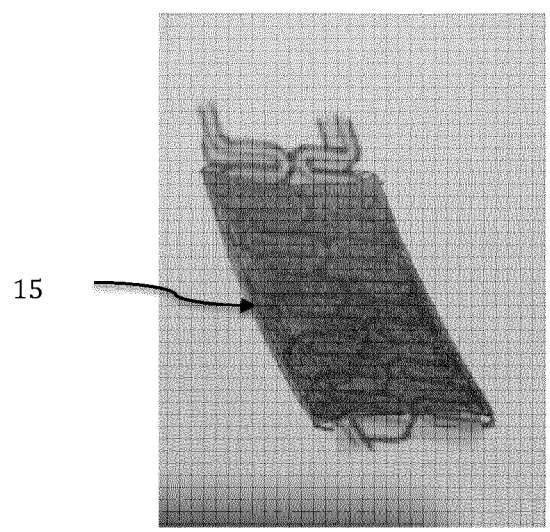

FIG. 34 illustrates the wavy lines of FIG. 33 surrounded by a sleeve.

Figure 35:
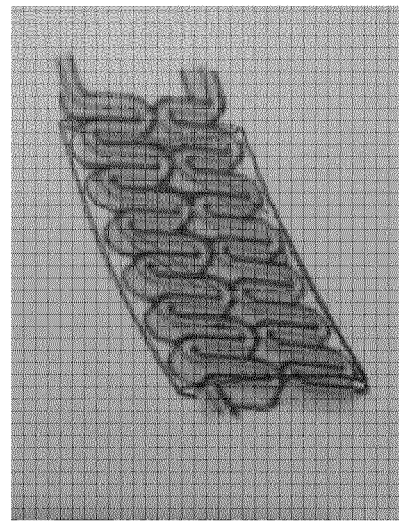

FIG. 35 illustrates the wavy lines of FIG. 33 surrounded by a more transparent sleeve.

Figure 36:
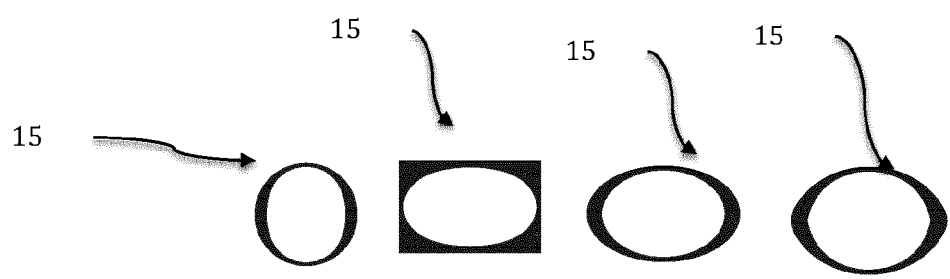

FIG. 36 shows different sleeve sections.

Figure 37:
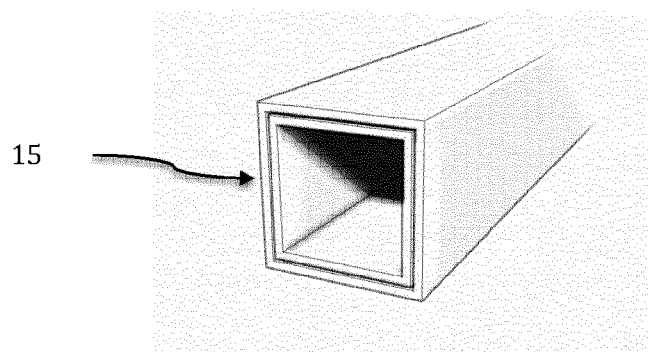
Figure 37:
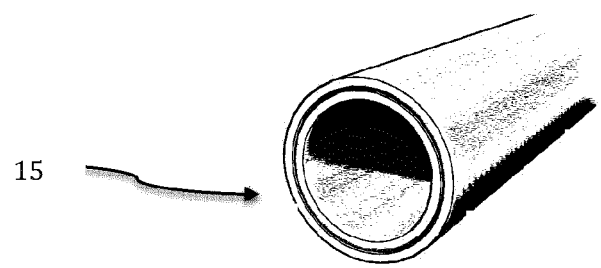
Figure 37:
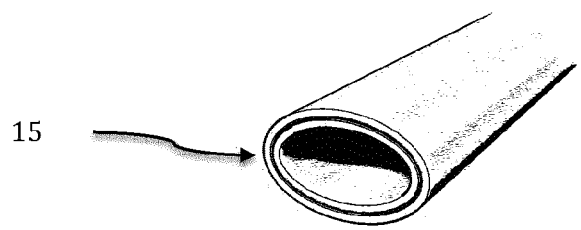

FIGS. 37A to 37C represent different sleeve shapes.

Figure 38:
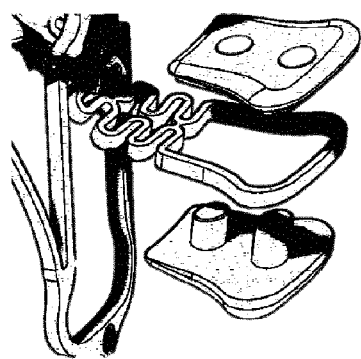
Figure 38:
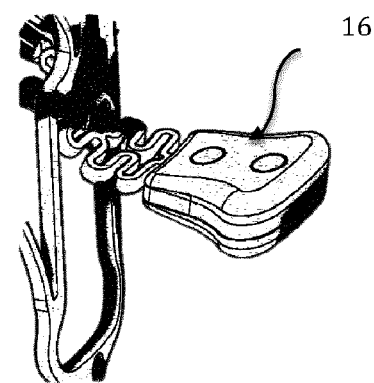

FIGS. 38A and 38B represent a protection cap made of two elements.

Figure 39:
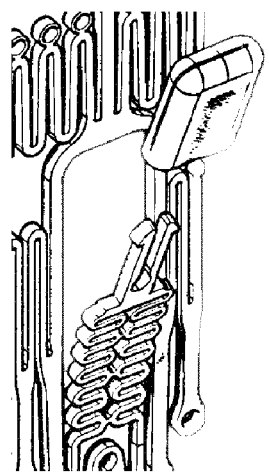
Figure 39:
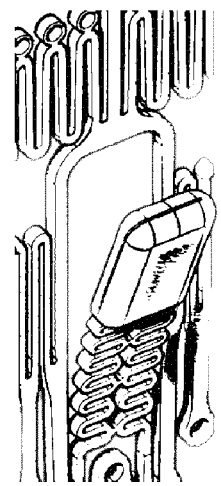
Figure 40:
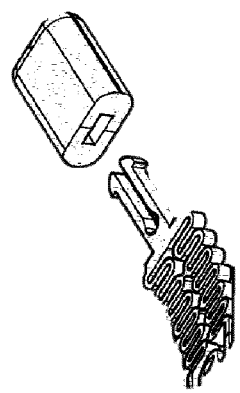
Figure 40:
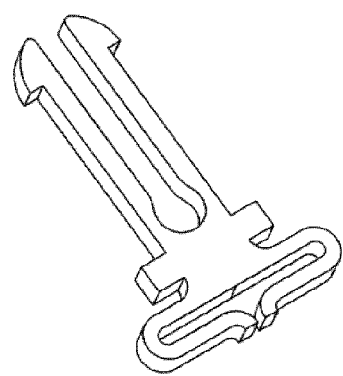
Figure 40:
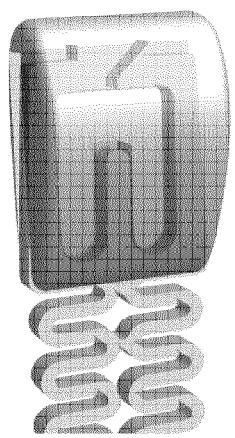
Figure 40:
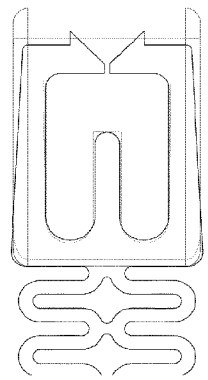
Figure 42:
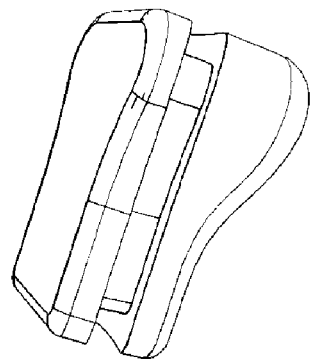
Figure 43:
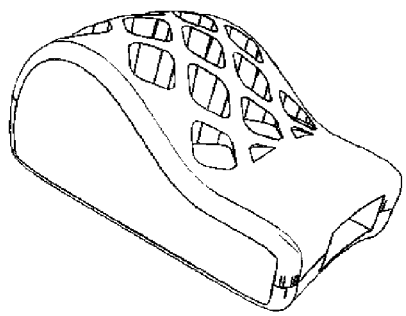
Figure 43:
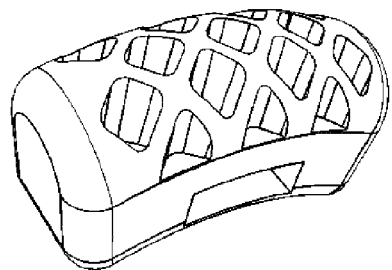
Figure 43:
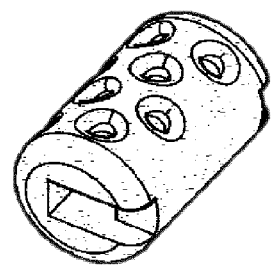
Figure 44:
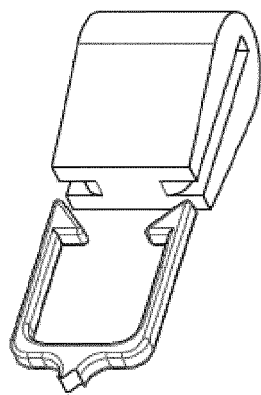
Figure 44:
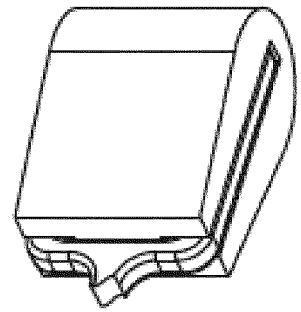
Figure 44:
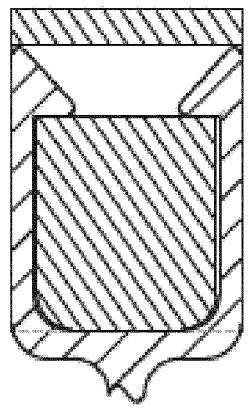
Figure 44:
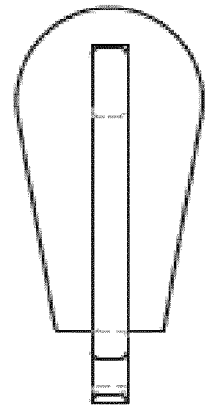

FIGS. 39A and 39B represent a protection cap made of one single element.

FIGS. 40A to 40D show some embodiments for fixing a cap to an extension body.

FIGS. 41A and 41B represent a cylindrical protection cap.

FIGS. 42A to 44D represent different protection caps.

Figure 45:
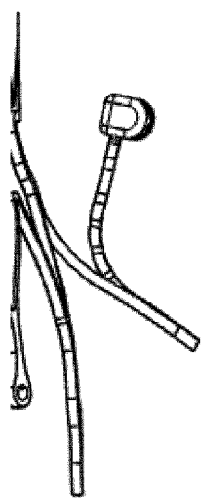
Figure 45:
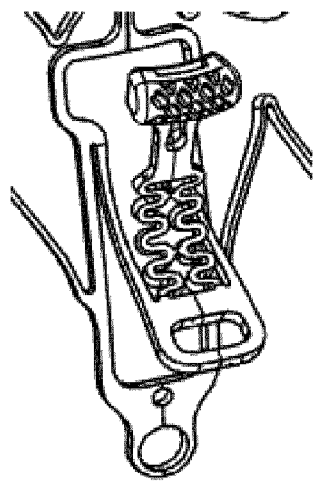

FIGS. 45A and 45B show an embodiment of a stent with a single posterior extension body.

Figure 46:
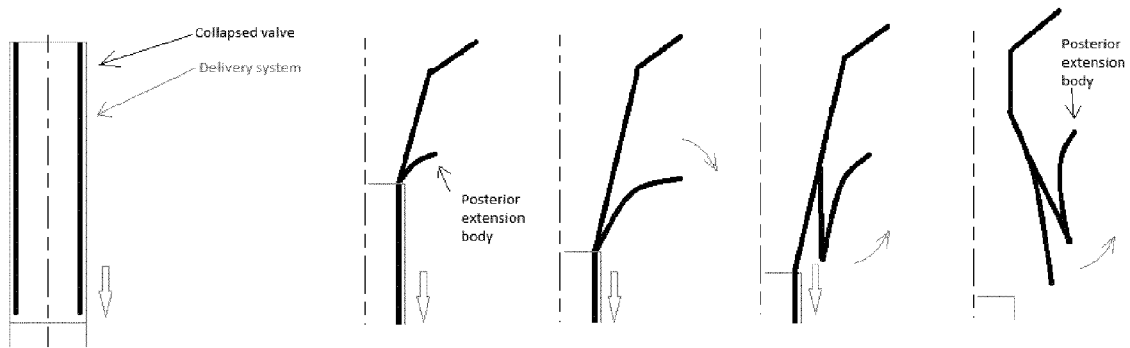
Figure 47:
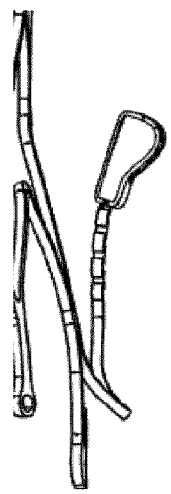
Figure 47:
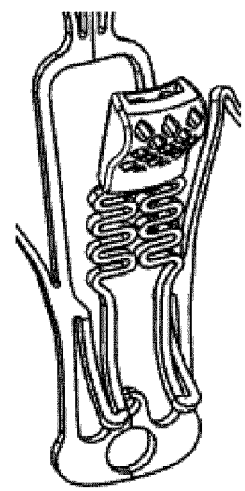
Figure 47:
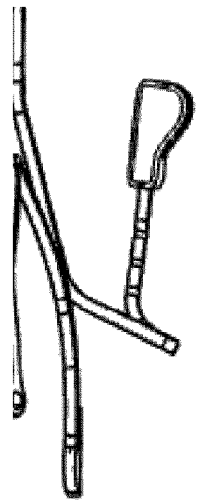
Figure 47:
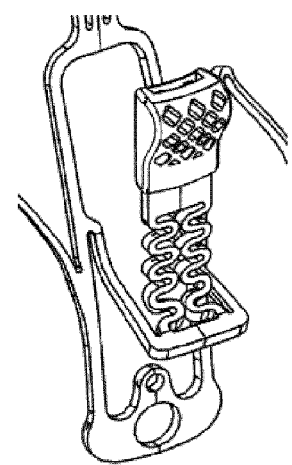
Figure 48:
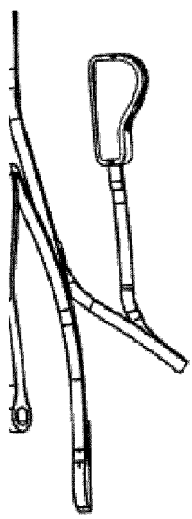
Figure 48:
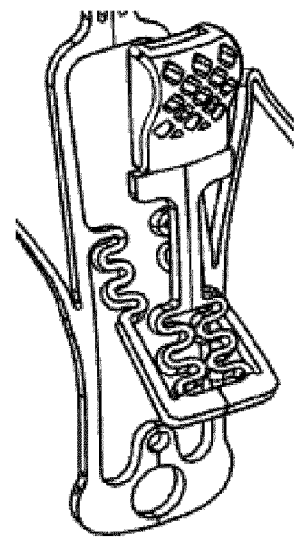
Figure 49:
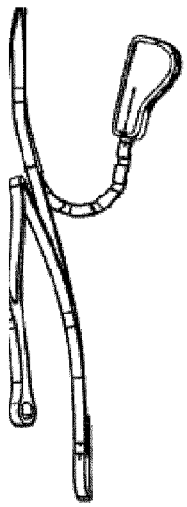
Figure 49:
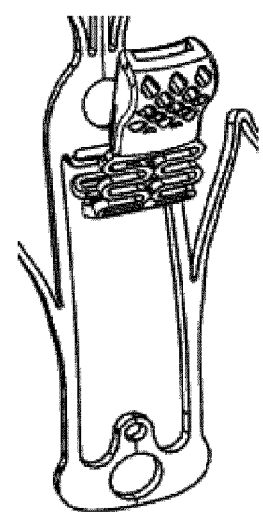
Figure 50:
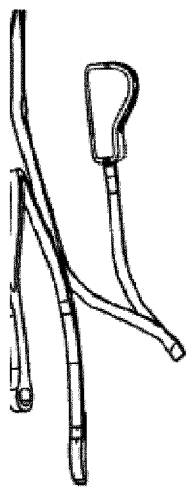
Figure 50:
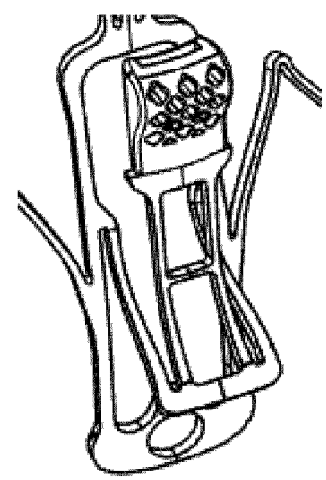
Figure 55:
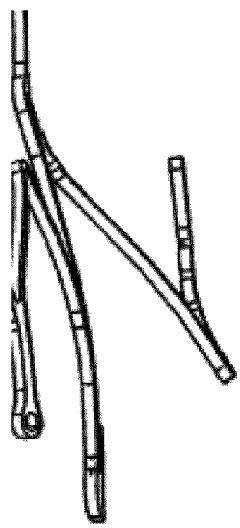
Figure 55:
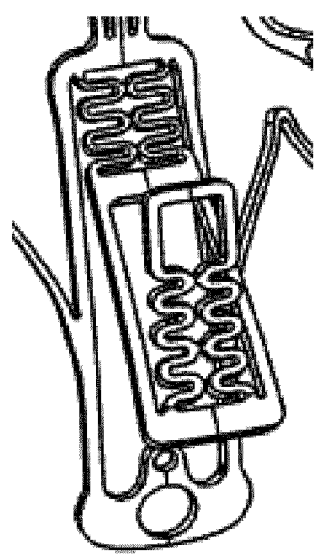
Figure 56:
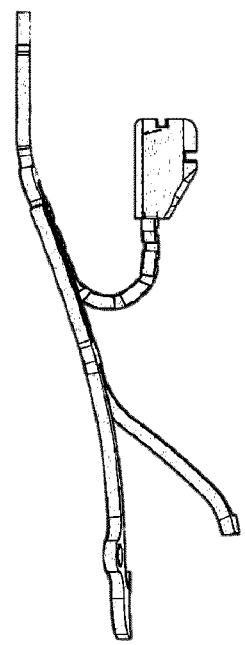
Figure 56:
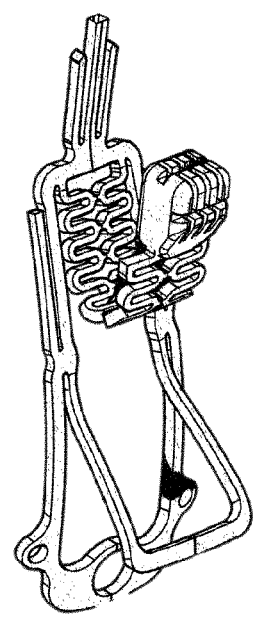

FIG. 46 schematically illustrates the deployment of the stent from a delivery system (in particular the posterior extension body).

FIGS. 47A to 56B illustrate different embodiments of extensions bodies or engagement members according to the invention.

NUMERICAL REFERENCES USED IN THE FIGURES

1. Stent
2. Stent sub annular anterior side
3. Stent sub annular posterior side
4. Anterior native valve engagement member
5. Engagement member foldable portion
6. Wavy line
7. Bridge
8. Blade
9. Linking segment
10. Extension body (10'. Trigone Extension body, 10". Posterior wall extension body, 10'''. extension body locking system for native anterior leaflet)
11. Posterior native valve engagement member
12. Anterior native leaflet
13. Stent sub annular lateral side
14. Windows frame
15. Sleeve
16. Cap The stent 1 shown in FIGS. 2 and 3 is in an expanded state, with one engagement member 4 at the anterior side and its locking system (commissure-commissure line) of the stent 1.

The engagement member 4 is oriented along a direction that is parallel to the wall of the stent body (see FIG. 2).

FIG. 4 shows a portion of the stent 1, in a flattened configuration before its conformation into a collapsed state. The engagement member 4 is in its flat status (0° angle) as it happens when the valve is loaded into the delivery system.

In this example the sub annular anterior side height added by the engagement member 4 length is equivalent or shorter than the sub annular posterior side height 3.

FIG. 5 represents the grasping and retaining of an anterior native leaflet 12 at the middle leaflet segment A2, with an engagement member 4 and extension bodies 10''' (locking mechanism) according to the invention. In this example the engagement member 4 locks the anterior leaflet 12 and the extension bodies 10''' are placed behind it. This solution, retaining the middle segment A2 of the native leaflet 12, is aimed at anchoring it in a portion where no chordae are present thus minimizing the risk of cordage ruptures.

FIG. 6 represents the leaflet 12 of FIG. 4 in a locked position. The locking mechanism is activated by the joint action of the extensions bodies 10'' and the engagement member 4. The extensions bodies grasp and hold the leaflet 12 and the engagement member 4 pinches and thus completely blocks the leaflet 12. The engagement member 4 locks the anterior leaflet 12 and the extension bodies 10''' are placed ahead of it. In both configurations the locking mechanism works.

FIG. 7 shows different orientations of the engagement member 4 when the stent 1 is in an expanded state. The engagement member 4 is part of the stent structure. In this figure different opening angles of the engagement member 4 are showed. In particular, in picture 7C and 7D show that the stent pillar sustaining the engagement member 4 can be bent outward with a variable angle (0° to 40°) thus allowing it to be more effective in grabbing the anterior mitral leaflet 12.

FIG. 8 illustrates another example showing the fixation of an engagement member 4 to the stent body. In this case the engagement member 4 is not initially part of the stent structure. This is an alternative design solution in order to reduce the torsion of the engagement member 4 when is opened. This solution adopts the use of a wire, made of Nitinol or another metallic alloy, to be welded or crimped over supports obtained from the stent's structure. In this configuration the anchoring of the engagement member 4 to the stent 1 can be obtained with different technologies.

The stent 1 illustrated in FIG. 9 is in a collapsed state. Here also the engagement member length does not increase the length of the stent 1. The distal end of the engagement member 4 is at the same level of the distal end of the posterior segment of the stent 1.

The stent 1 illustrated in FIG. 10 is in a collapsed state. Here also the engagement member length (anterior and posterior) does not increase the length of the stent 1. The distal end of the anterior engagement member 4 and the posterior engagement member 11 are at the same level of the distal end of the stent 1 and can be released at the same heights and time during deployment.

FIG. 11 illustrates an example of the movement of the engagement members 4 or 11 when released from the delivery system according to the invention, in an intermediate position.

FIG. 12 shows the engagement members 4 or 11 of FIG. 10 in a final position. The stent 1 illustrated in FIG. 13A contains one anterior and one posterior engagement members 4 and 11, both being located on the distal end of the stent ventricular portion. FIG. 13B shows another configuration of the posterior engagement member 11 originating from the sub-annular segment of the stent. In this configuration the posterior stent side 3 is absent.

In the example of FIG. 14 the stent 1 contains one anterior engagement member 4 located at the distal end of the anterior part of the stent ventricular portion and one posterior engagement member 11 located at mid height of the posterior side 3. This representation is in according with the anatomic characteristics of the mitral valve. The anterior leaflet 12 is longer than the posterior leaflet; consequently the engagement members 4 and 11 should be released at different heights.

In the example of FIG. 15 two engagement members 4 are located on the stent anterior side.

In the example of FIG. 16 the stent 1 contains two engagement members located 4 on the anterior side and two engagement members 11 located on the posterior side.

FIG. 17 shows another engagement member 4 according to the invention. In this case the engagement member 4 and/or 11 is (are) fixed to the stent 1 through a segment 9 via two parallel wavy lines 6.

FIG. 18 shows another engagement member 4 and/or 11 according to the invention, which extends from the stent body. The engagement member 4 and/or 11 is/are part of the same memory shape material, e.g. nitinol, than the one, which constitutes the stent body. Such a configuration prevents from any risk of corrosion or galvanic forces.

FIG. 19 shows the engagement member 4 of FIG. 16 with the extension bodies 10''' highlighted (in bold).

Figure 20:
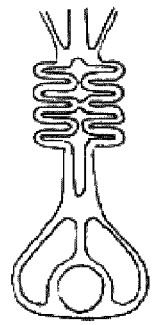

FIG. 20 shows another engagement member according to the invention. In this example the wavy lines 6 are linked to each other through a bridge 7.

Figure 21:
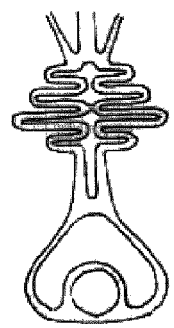

FIG. 21 shows another engagement member according to the invention. The wavy lines 6 are linked to each other and asymmetric. The continuity with the anterior part of the stent is made by three elements, a main one and two secondary.

Figure 22:
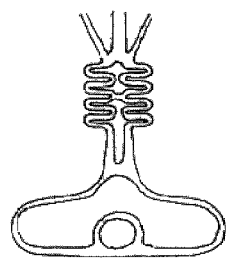

FIG. 22 shows another engagement member according to the invention.

Figure 23:
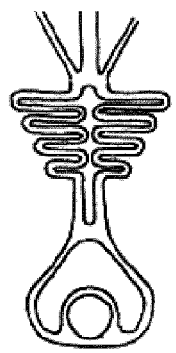

FIG. 23 shows another engagement member according to the invention.

Figure 24:
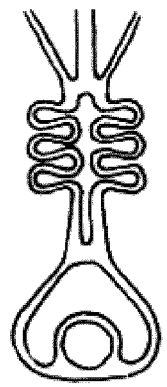

FIG. 24 shows another engagement member according to the invention.

Figure 25:
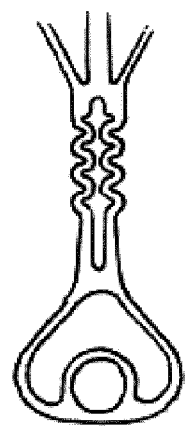

FIG. 25 shows another engagement member according to the invention. The wavy lines 6 in this example are less pronounced and more linear.

Figure 26:
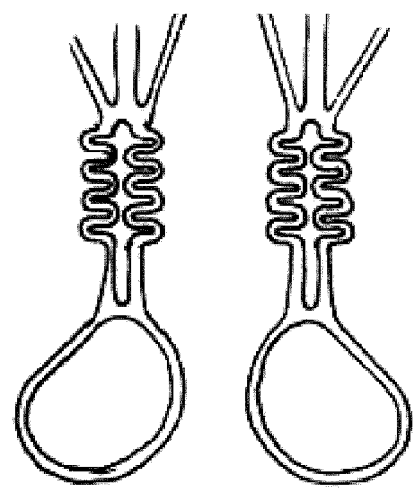

FIG. 26 shows two engagement members 4 according to the invention, the blades 8 are symmetrically oriented along different directions.

FIG. 27, shows an atrial view of the stent 1 that contains one anterior 4 and one posterior 11 engagement members, the anterior member 4 being located on the distal end of the stent ventricular portion and the posterior member 11 originating from the sub-annular segment of the stent 1. Four extension bodies, two to the anterior side (trigones extension bodies 10') and two to the posterior side (posterior side extension bodies 10"), originate from the sub-annular segment.

FIG. 28, shows the lateral view of the stent 1 a contains one anterior and one posterior engagement members 4 and 11, the anterior being located on the distal end of the stent ventricular portion and the posterior engagement member 11 originating from the sub-annular segment of the stent 1. Two extension bodies, one to the anterior side 10' and one to the posterior side 10", originate from the sub-annular segment and come out from the stent windows frame 14.

FIG. 29, anatomical drawing showing the sub annular groove, i.e. where the stent sub annular side is located.

Figure 1:
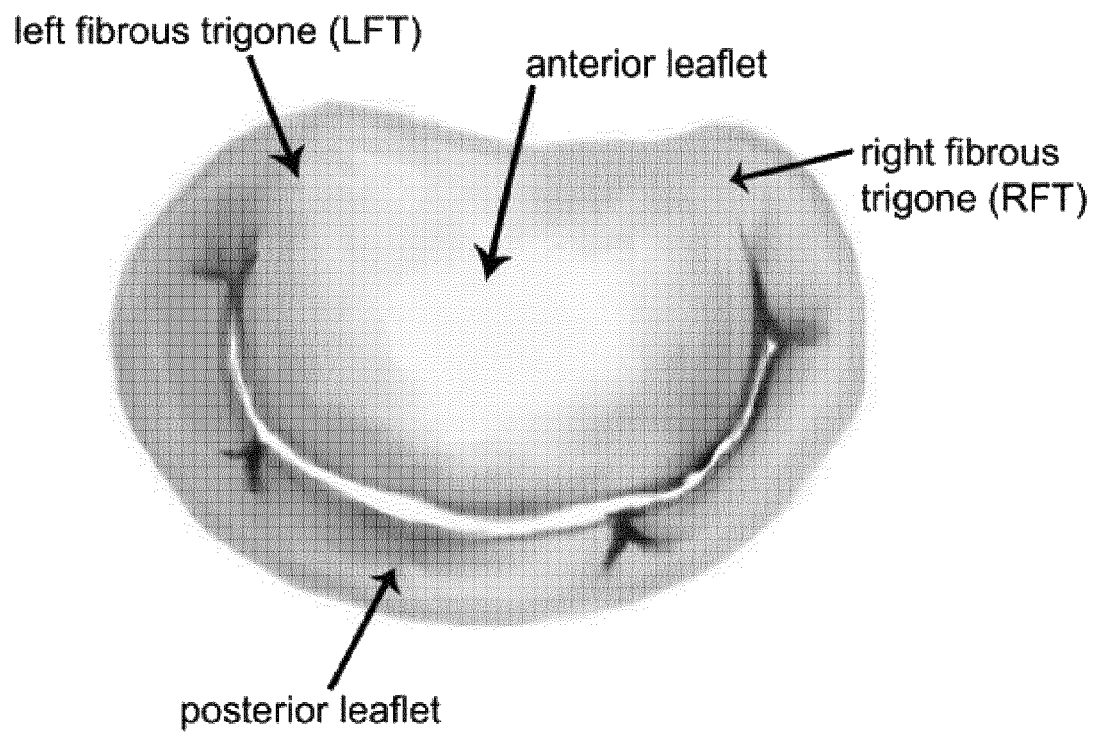
FIG. 1 represents a native mitral valve.

FIGS. 30 A and B Trigone extension body: Located in correspondence of the native mitral trigones (border transition between the anterior leaflet and posterior leaflets P1 and P3). See FIG. 1. This extension body is in contact with the fibrous tissue of the native trigones stabilizing the bioprosthesis and providing an effective anchoring function. It is attached to the upper or lower portion of the window's frame and bent outward. The extension body is bent out 5° to 45° if it is originated from the lower part of the window's frame (FIG. 30A). On the contrary the bending has an angle preferably ranging between 30° and 120° if the extension body is originated from the upper part of the window's frame (FIG. 30B).

FIG. 31. Posterior extension body: A single extension body anchoring the stent from the posterior side grabbing the middle portion of the native posterior leaflet P2, where no chordae are present, and getting in contact with the myocardial tissue at level of the posterior sub-annular groove (FIG. 29). Two anchoring extensions bodies, positioned at level of the posterior sub-annular recess preferably in correspondence to the clefts (FIGS. 1 and 29) of the native posterior leaflet (P1/P2 and P3/P2) without the need to grab the posterior leaflet. The posterior extension body is attached to the upper or lower portion of the window's frame and bent outward. If the extension body is attached to the lower portion of the window's frame the bending angle can vary from 5° to 45° (FIG. 31A). On the contrary if the extension body is attached to the upper part, the bending angle can range between 90° and 180° (FIG. 31B).

Another type of posterior anchoring system can be obtained with double extension bodies originated from one single windows frame. The first body bent outward between 5° and 45° with a function of balance arm originated from the upper part of the windows frame and the second body bent outward between 90° and 180° always from the upper part of the window frame (FIG. 31C) with the function of grabbing the posterior native leaflet and seating at level of the mitral groove.

An alternative anchoring system is when the second body is originated from the middle or lower part of the first body and bent outward between 5° and 45°.

Plurality of extension bodies: the prosthesis can be anatomically anchored with a plurality of extension bodies originated from the stent structures and distributed all around the circumference of the stent. The configuration of such extension bodies can be similar to those for the anterior or the posterior portion of the cardiac wall or those for the trigones or a mix of such extension bodies.

Another original aspect of the invention relates to the way the anchoring system is obtained.

The anchoring system is directly obtained from the stent configuration without bending structures protruding over the stent profile or external parts attached to the stent with different methods.

With exception of the anterior engagement member and in same embodiments of the posterior engagement member, the trigones and posterior extension bodies can be originated from the upper, lower or lateral portion of the window's frame with one or more insertion points (preferably 1 or 2). The extension bodies may be bent outward at different angles in order to obtain the optimal anchoring to the cardiac tissues. Some examples are shown on FIGS. 32A to 32D.

The posterior engagement member can be originated from a windows frame 14 or in the same way of the anterior engagement member without frame.

Figure 32:
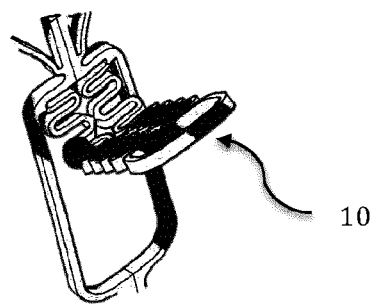
Figure 32:
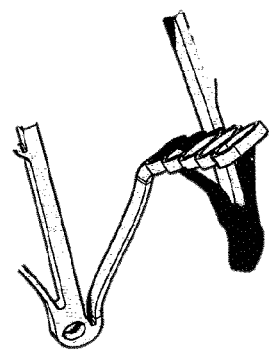
Figure 32:
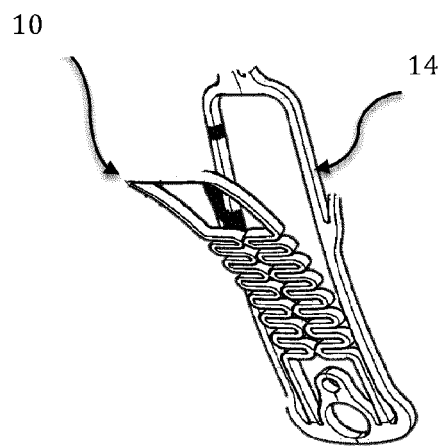
Figure 32:
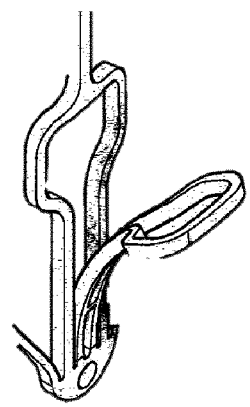

An extension body preferably comprises two important elements. A wavy-line connection-bridge between the stent body (frame window) and a flat blade (also named "paddle"). It can be mentioned that in some embodiments the extension body can be constituted only by flat blade (FIGS. 32B and 32D). The blade and the wavy-line may be covered by a sleeve and distally protected by a protection cap. The function of the wavy-line connection bridge is to provide the necessary outward bending of the extension bodies from the windows frames (even at high angles close to 180°) minimizing the fatigue stress on the stent's material. The paddle or the protection cap are designed to get in contact with the cardiac tissue without damaging it and providing a fast and homogeneous tissue fibrosis aimed at stabilizing the anchoring of the valve in the time.

The wavy-line connection-bridges, in particular those ones aimed at grabbing the native leaflets (anterior and posterior engagement members), may lead to tears of the leaflet tissue after cyclic stress (FIG. 33). To solve this potential complication a sleeve 15 may advantageously cover each connection-bridge, which is flexible enough in order to not interfere with the flexibility and the anchoring movement of the extension bodies. This solution may be used for all wavy-line or flat blade connection-bridges present on the extension bodies of the stent. A sleeve can be obtained from a flat surface material wrapped and stitched around the wavy-line (FIG. 34) or from a tubular structure mounted over the wavy-line by simple dilation taking advantage of their elastic properties (FIG. 35). The material can be biologic or synthetic, with or without biodegradation properties. The biologic materials may consist of pericardial tissue from different origins (bovine, porcine, etc. . . . ). The synthetic materials can be fabric ones (woven or knitted) such as polyester or polytetrafluoroethylene fabrics or felt or non fabric ones such a continuous polymeric films with proven long-term biocompatibility in micro-tubular shape obtained with different technologies (e.g. dipping, electro-spinning or extrusion without limitation). The preferred materials may consist of polyurethane, carbonated or not, silicone or polytetrafluoroethylene. The micro-tubular structures can be obtained in circular, ovoid, elliptical or rectangular section with an asymmetrical thickness (thicker on the lateral sides to reduce the risk of fatigue tears) (FIG. 36). The wall of these micro-tubular structures, besides having an asymmetrical thickness, can be composed by different number of layers, different materials with different hardness in a broad range of possible technical solutions (FIG. 37A to 37C). The thickness of the wall can range, for example, from 5-10 μm to 100-200 μm.

The distal part of the extension bodies coming directly in contact with cardiac tissue may lead to an acute and chronic injury to the surrounding tissues. To overcome this potential issue the extension body free end may be covered or replaced by a protection cap 16. A cap provide of more homogenous distribution of the cyclic peak systolic pressure over a larger surface thus eliminating the potential injury to the cardiac tissues. A protection cap may consist of two parts and mounted on both sides of the paddle (FIGS. 38A and 38B), in a sandwich-like configuration, or better realized in one single piece (FIGS. 39A, 39B). In this last case it is securely anchored to a specifically designed distal end of the extension body using different technologies (mechanical anchoring, gluing, dipping, on-site molding, ultrasound welding, laser welding, etc. . . . ). A mechanical anchoring can be realized designing the extension body flat blades, for example, like a double arrow (FIGS. 40A to 40C) in order to grant a secure attachment of the protection caps, after mounting, without the possibility to remove them. Another technical solution to get a mechanical anchoring is represented by a cylindrical shape protection cap retained by two lateral arms as described in FIGS. 41A and 41B. The cylindrical protection cap can be firm or in alternative can be able to rotate around its longer axis. The gluing can be applied alone or in association to mechanical anchoring. Various solutions can be envisaged using Ciano-Acrylic biocompatible glues resistant to long-term exposition to water and to tissues' foreign body response. The dipping technique can be obtained shaping the distal end of the extension bodies with a paddle-like shape progressively coated with a polymer till obtaining the desired rounded shape. The welding, also potentially associated with mechanical anchoring or gluing, can be adopted. In particular, the ultrasonic welding can be applied to a mechanically anchored protection cap (FIGS. 42A to 42E).

They can be realized with different biomaterials (e.g. polyacetalic resin, polyurethane, polyetheretherketone, polyvinylidenefluoride, Silicone, polytetrafluoroethylene, ceramic, metal, etc. . . . ), different technologies (machining, pressure or injection moulding, syntherization, dipping, etc. . . . ), textured surfaces and shapes (FIGS. 43A to 43C). The texture of the protection cap's surface can be modulated according to the chosen material, its rigidity and the nature of the tissues to which it comes in contact. The surface roughness of the protection cap is very important because acutely helps enhancing the grip of the anchoring system and chronically it provides an adequate substrate for tissue ingrowth granting a long-term retention of the stent (FIGS. 44A to 44D). A drug-eluting protection cap can be used to obtain an acceleration of the scar formation or any other form of benefit as reduction of infection, thrombi formation etc. An echocardiographic or fluoroscopic markers can be added to facilitate valve deployment and to facilitate caps' identification after implant. They can be also manufactured with radiopaque materials.

The embodiments discussed below do refer to posterior extension bodies.

A single posterior extension body is used to anchor the stent from the posterior side, grabbing the middle portion of the native posterior leaflet, where no chordae are present, and getting in contact with the myocardial tissue at level of the posterior sub-annular recess. An alternative solution is based on two or more extension bodies anchoring the posterior sub-annular recess (FIG. 29) in correspondence to the clefts of the posterior leaflet (P1/P2 and P3/P2) without the need to capture the native posterior leaflet (FIG. 18C).

FIGS. 45A and 45B show an embodiment of a stent with a single posterior extension body.

FIG. 46 schematically illustrates the deployment of the stent from a delivery system (in particular the posterior extension body).

FIGS. 47 to 56 illustrate different embodiments of extensions bodies or engagement members according to the invention.

The invention is of course not limited to the illustrated examples. Any suitable geometry or material can be used for the stent the extension bodies and the engagement member(s).

The invention claimed is:

1. An atrio-ventricular valve stent having a tubular shape comprising:
   a sub annular anterior side;
   a sub annular posterior side; and
   a plurality of sub annular lateral sides,
   wherein the sub annular anterior side includes a self-folding native leaflet engagement member that forms a straight extension of the sub annular anterior side towards an outflow direction when the stent is in a collapsed state and folds when the stent is in an expanded state, such that the self-folding native leaflet engagement member bends backwards towards an inflow direction by a bending angle of more than 90°,
   wherein each one of the plurality of sub annular lateral sides is longer than the sub annular anterior side when the stent is in the expanded state, and
   wherein the valve stent has an outflow end that includes an axially-extending recess at the sub annular anterior side, the self-folding native leaflet engagement member arranged within the axially-extending recess extending in the outflow direction when the valve stent is in the collapsed state.

2. The atrio-ventricular valve stent according to claim 1, wherein each one of the plurality of sub annular lateral sides is longer than the sub annular posterior side when the stent is in the expanded state.

3. The atrio-ventricular valve stent according to claim 1, wherein the sub annular posterior side is longer than the sub annular anterior side when the stent is in the expanded state.

4. The atrio-ventricular valve stent according to claim 1, wherein the sub annular posterior side is shorter than the sub annular anterior side when the stent is in the expanded state.

5. The atrio-ventricular valve stent according to claim 1, wherein the sub annular posterior side and the sub annular anterior side have a same length when the stent is in the expanded state.

6. The atrio-ventricular valve stent according to claim 1, the stent having a D-shaped cross section.

7. The atrio-ventricular valve stent according to claim 1, wherein the self-folding native leaflet engagement member and the sub annular anterior side are linked via a single connection element of the sub annular anterior side of the valve stent.

8. The atrio-ventricular valve stent according to claim 1, wherein the self-folding native leaflet engagement member includes a foldable portion having at least one wavy line.

9. The atrio-ventricular valve stent according to claim 8, wherein the at least one wavy line comprises:
a first and a second symmetric wavy line,
wherein a wave formed by the first symmetric wavy line is linked to a wave of the second symmetric wavy line by a bridge.

10. The atrio-ventricular valve stent according to claim 9, wherein the bridge is covered by a sleeve.

11. The atrio-ventricular valve stent according to claim 1, wherein the engagement member includes a free end that is flared.

12. The atrio-ventricular valve stent according to claim 1, further comprising:
an anterior native valve locking system including a first self-orienting extension body that also forms an integral part of the stent and that is located within the sub annular anterior side,
wherein the first self-orienting extension body coincides with the sub annular anterior side when the stent is in the collapsed state and the first self-orienting extension body is oriented in another direction when the stent is in the expanded state.

13. The atrio-ventricular valve stent according to claim 12, wherein the first self-orienting extension body is oriented at 30° towards the inflow direction when the stent is in the expanded state.

14. The atrio-ventricular valve stent according to claim 12 further comprising:
a posterior native valve locking system made of a second self-orienting extension body that also forms an integral part of the stent and that is located within the sub annular posterior side, the second self-orienting extension body coinciding with the sub annular posterior side when the stent is in a collapsed state and the second self-orienting extension body oriented in another direction when the stent is in the expanded state.

15. The atrio-ventricular valve stent according to claim 12, wherein the first self-orienting extension body is surrounded by a window frame, and wherein one end of the extension body is fixed to one side of the window frame.

16. The atrio-ventricular valve stent according to claim 15, wherein the first self-orienting extension body is fixed to an upper side or to a lower side of the window frame.

17. The atrio-ventricular valve stent according to claim 15, wherein the window frame coincides with a wall of the stent when the stent is in the collapsed state and does not coincide with the wall of the stent when the stent is in the expanded state.

18. The atrio-ventricular valve stent according to claim 17, wherein the first self-orienting extension body forms an angle between 150° and 180° with the wall of the stent when the stent is in the expanded state.

19. The atrio-ventricular valve stent according to claim 15, wherein the first self-orienting extension body forms an angle between 60° and 120° with the frame when the stent is in the expanded state.

20. The atrio-ventricular valve stent according to claim 15, wherein the first self-orienting extension body forms an angle between 5° and 30° with the frame when the stent is in the expanded state.

21. The atrio-ventricular valve stent according to claim 12, wherein the first self-orienting extension body is entirely made of a flat blade.

22. The atrio-ventricular valve stent according to claim 21, wherein an end of the flat blade is covered by a cap.

23. The atrio-ventricular valve stent according to claim 1 further comprising:
a plurality of engagement members.

24. The atrio-ventricular valve stent according to claim 1 further comprising:
a native posterior leaflet engagement member located on the sub annular posterior side.

25. The atrio-ventricular valve stent according to claim 1, wherein the bending angle of the self-folding native leaflet engagement member in the expanded state is in a range between 160° to 180°.

26. The atrio-ventricular valve stent according to claim 1, wherein the self-folding native leaflet engagement member forms an integral part of the stent.

27. The atrio-ventricular valve stent according to claim 1, wherein a location of connection of the self-folding native leaflet engagement member to the sub annular anterior side is closest to an inflow end of a stent wall, and a location of the stent wall on the sub annular posterior side that is radially opposite to the axially-extending recess is farthest from the inflow end of the stent wall.

28. The atrio-ventricular valve stent according to claim 1, wherein in the collapsed state, the self-folding native leaflet engagement member forming the straight extension does not increase an overall length of the valve stent as compared to the expanded state where the self-folding native leaflet engagement member is bent backwards.

* * * * *